(12) United States Patent
Yoshida et al.

(10) Patent No.: US 8,096,942 B2
(45) Date of Patent: Jan. 17, 2012

(54) ENDOSCOPE BALLOON CONTROL DEVICE

(75) Inventors: Takatoshi Yoshida, Hachioji (JP); Sumihiro Uchimura, Sagamihara (JP); Akira Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 904 days.

(21) Appl. No.: 11/545,678

(22) Filed: Oct. 10, 2006

(65) Prior Publication Data
US 2007/0055101 A1 Mar. 8, 2007

Related U.S. Application Data

(63) Continuation of application No. PCT/JP2005/006874, filed on Apr. 7, 2005.

(30) Foreign Application Priority Data

Apr. 9, 2004 (JP) ................................. 2004-115849

(51) Int. Cl.
*A61B 1/04* (2006.01)
*A61B 1/00* (2006.01)

(52) U.S. Cl. .................... 600/116; 600/115; 600/118

(58) Field of Classification Search ............... 600/115, 600/116, 118, 159, 114, 119; 604/99.01, 604/100.01–100.03, 101.05
See application file for complete search history.

(56) References Cited

U.S. PATENT DOCUMENTS

| | | | |
|---|---|---|---|
| 3,720,199 A * | 3/1973 | Rishton et al. ................ | 600/18 |
| 4,040,413 A * | 8/1977 | Ohshiro ......................... | 600/116 |
| 4,676,228 A * | 6/1987 | Krasner et al. ................. | 600/116 |
| 4,690,131 A * | 9/1987 | Lyddy et al. ................... | 600/115 |
| 4,934,786 A * | 6/1990 | Krauter ......................... | 385/118 |
| 5,004,472 A * | 4/1991 | Wallace ......................... | 606/194 |
| 5,090,259 A * | 2/1992 | Shishido et al. .............. | 73/866.5 |
| 5,243,967 A * | 9/1993 | Hibino .......................... | 600/109 |
| 5,749,853 A | 5/1998 | O'Donnell et al. | |

(Continued)

FOREIGN PATENT DOCUMENTS

JP 06-217935 8/1994

(Continued)

OTHER PUBLICATIONS

Yamamoto, Hironori, Endoscope, Publication date: Oct. 15, 2002, Published by JPO, 8 pages of document, Retrieved from PAJ on Aug. 16, 2010 via http://dossier1.ipdl.inpit.go.jp/AIPN/odse_call_transl... .*

*Primary Examiner* — Anhtuan Nguyen
*Assistant Examiner* — Alireza Nia
(74) *Attorney, Agent, or Firm* — Scully, Scott, Murphy & Presser, P.C.

(57) ABSTRACT

A first and a second pumps for supplying a gas to a balloon for fixation mounted at an outer circumference portion at a tip end portion of an insertion portion of an endoscope and a balloon for fixation mounted at an outer circumference portion at a tip end portion of an overtube into which the endoscope is inserted and a control portion for controlling pressure in the respective balloons by operating the first and the second pumps are provided, and the control portion controls display of balloon inflation/deflation display portions and balloon during operation display portions of a remote controller on the basis of inflation-state information detected by a state detection output portion detecting inflation states of the respective balloons.

19 Claims, 18 Drawing Sheets

U.S. PATENT DOCUMENTS

| | | | |
|---|---|---|---|
| 5,788,688 A * | 8/1998 | Bauer et al. | 606/1 |
| 5,872,527 A * | 2/1999 | Yanagisawa | 341/22 |
| 6,007,482 A * | 12/1999 | Madni et al. | 600/115 |
| 6,051,016 A * | 4/2000 | Mesaros et al. | 606/202 |
| 2001/0020150 A1 * | 9/2001 | Ravo | 604/101.01 |
| 2003/0208222 A1 * | 11/2003 | Zadno-Azizi | 606/194 |

FOREIGN PATENT DOCUMENTS

| | | |
|---|---|---|
| JP | 2001-340462 | 12/2001 |
| JP | 2002-301019 | 10/2002 |
| JP | 2003-144378 | 5/2003 |
| JP | 2005-007030 | 1/2005 |
| WO | WO 86/07249 | 12/1986 |

* cited by examiner

ENDOSCOPE BALLOON CONTROL DEVICE

CROSS REFERENCE TO RELATED APPLICATION

This application is a continuation application of PCT/JP2005/006874 filed on Apr. 7, 2005 and claims benefit of Japanese Application No. 2004-115849 filed in Japan on Apr. 9, 2004, the entire contents of which are incorporated herein by this reference.

BACKGROUND OF THE INVENTION

1. Field of the Invention

The present invention relates to an endoscope balloon control device and an endoscope balloon control device which can make an operator recognize an inflation state of a balloon provided on the outer circumference at a tip end portion of an insertion portion of an endoscope and a balloon provided on the outer circumference of a tip end portion of an insertion portion of an overtube.

2. Description of the Related Art

In a digestive tract inspection, an endoscope inspection is often used in general. In such an endoscope inspection, when an insertion portion of an endoscope is to be inserted into a deep digestive tract such as a small intestine, for example, if only the insertion portion is pushed in, a force is hard to be transmitted to the tip end of the insertion portion due to complicated bending of the intestinal tract, and insertion into a deep portion is difficult. If the endoscope is withdrawn to extend excess bending or deflection of the endoscope generated by insertion into the deep portion, for example, the tip end of the insertion portion is also withdrawn, and bending or deflection can not be eliminated and insertion into the deep portion becomes difficult.

Then, such an endoscope is proposed that a balloon is mounted on the outer circumference of the tip end portion of the insertion portion of the endoscope and the balloon is inflated and temporarily fixed to the intestinal tract so as to prevent removal of the tip end portion of the insertion portion when the excess bending or deflection generated at the endoscope is to be extended.

Also, in the prior art, such an endoscope device is proposed that an overtube through which the insertion portion of the endoscope is inserted is provided, while a balloon is provided on the outer circumference of the tip end portion of this overtube and this balloon and the balloon of the endoscope are inflated/deflated as appropriate so that operating performance of the endoscope device is improved. In Japanese Unexamined Patent Application Publication No. 2002-301019, for example, an endoscope is disclosed in which for the balloon of the endoscope and the balloon of the overtube, an air pressure in each balloon is measured by a measuring device and air is supplied from a pump device while pressure in each of the balloons is controlled.

SUMMARY OF THE INVENTION

The endoscope device of the present invention comprises a pump for supplying/discharging a gas to/from a balloon for fixation mounted at the outer circumference portion of the tip end portion of an insertion portion of an endoscope, a control portion for controlling the pressure in the balloon, an inflation-state detection portion for detecting the inflation state of the balloon, and an inflation-state information output portion for outputting inflation-state information for display on the basis of a detection result by the inflation-state detection portion.

BRIEF DESCRIPTION OF THE DRAWINGS

FIG. 6 is an explanatory view showing a state where the balloon of the overtube is inflated and fixed to an intestinal tract.

FIG. 7 is an explanatory view showing a state where the endoscope is further inserted into the overtube from the state in FIG. 6.

FIG. 8 is an explanatory view showing a state where the balloon of the endoscope is inflated and fixed to the intestinal wall in the state in FIG. 7.

FIG. 9 is an explanatory view showing a state where the balloon of the overtube in the state in FIG. 8 is deflated and the overtube is further inserted.

FIG. 10 is an explanatory view showing a state where the tip end of the overtube is moved to the tip end portion of the endoscope from the state in FIG. 9.

FIG. 11 is an explanatory view showing a state where the balloon of the overtube in is inflated and fixed to the intestinal wall in the state in FIG. 10.

FIGS. 13 to 26 relate to a second embodiment of the present invention, in which FIG. 13 is a configuration diagram showing an entire configuration of an endoscope system to which an endoscope balloon control device is applied.

FIG. 14 is a block diagram showing an internal configuration of a video processor 5 shown in FIG. 13.

FIGS. 15 to 26 are for explaining display control operation by the endoscope balloon control device of this embodiment, in which FIG. 15 is a screen display view of a monitor corresponding to the operation state of the endoscope system.

FIG. 16 is a screen display view of the monitor corresponding to the operation state of the endoscope system.

FIG. 17 is a screen display view of the monitor corresponding to the operation state of the endoscope system.

FIG. 18 is a screen display view of the monitor corresponding to the operation state of the endoscope system.

FIG. 19 is a screen display view of the monitor corresponding to the operation state of the endoscope system.

FIG. 20 is a screen display view of the monitor corresponding to the operation state of the endoscope system.

FIG. 21 is a screen display view of the monitor corresponding to the operation state of the endoscope system.

FIG. 22 is a screen display view of the monitor corresponding to the operation state of the endoscope system.

FIG. 23 is a screen display view of the monitor corresponding to the operation state of the endoscope system.

FIG. 24 is a screen display view of the monitor corresponding to the operation state of the endoscope system.

FIG. 25 is a screen display view of the monitor corresponding to the operation state of the endoscope system.

FIG. 26 is a screen display view of the monitor when an emergency stop button is pressed down.

DETAILED DESCRIPTION OF THE PREFERRED EMBODIMENT(S)

Embodiments of the present invention will be described below referring to the attached drawings.

First Embodiment

Figure 1:
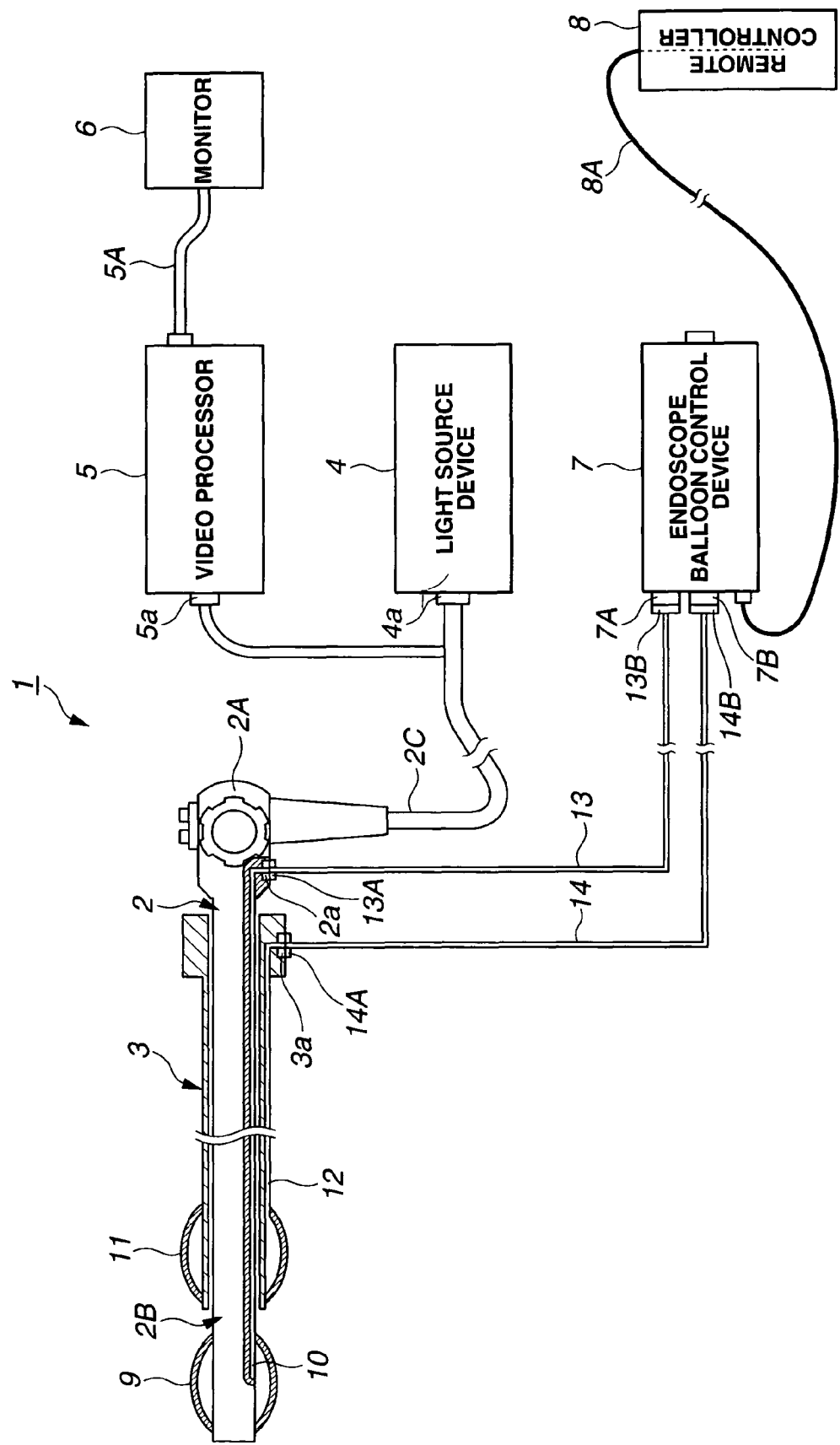
FIG. 1 relates to a first embodiment of the present invention and is a configuration diagram showing an entire configuration of an endoscope system to which an endoscope balloon control device is applied.

FIG. 1 relates to a first embodiment of the present invention and is a configuration diagram showing an entire configuration of an endoscope system to which an endoscope balloon control device is applied. As shown in FIG. 1, an endoscope system 1 having the endoscope balloon control device of this embodiment comprises an endoscope 2, an overtube 3, a light source device 4, a video processor 5, a monitor 6, an endoscope balloon control device 7, and a remote controller 8.

The endoscope 2 is used for an endoscope inspection of a digestive tract, for example, and has an insertion portion 2B to be inserted into a body cavity and an operation portion 2A provided at the base end side of this insertion portion 2B. Also, in the tip end portion of the insertion portion 2B, an observation optical system including an illumination optical and a charge coupled device (CCD), not shown, is provided so that a portion to be observed in the digestive tract of a subject is illuminated so as to obtain an observation image inside the digestive tract of the subject.

From the operation portion 2A, a universal cord 2C is extended. In this universal cord 2C, a signal line and a light guide cable, not shown, are provided. The base end portion of this universal cord 2C is connected to a connector 4a of the light source device 4, and a connector 5a of the video processor 5. By this, the illumination optical system in the endoscope 2 is supplied with illumination light from the light source device 4 through the light guide cable in the universal cord 2C for illuminating the portion to be observed and outputting a captured image signal inside the digestive tract outputted from the CCD to the video processor 5.

This type of endoscope 2 is used by being inserted into the overtube 3 during an operation. The configuration of the overtube 3 will be described later.

The light source device 4 is to supply illumination light to the illumination optical system provided to the endoscope 2 through a light guide (not shown) in the light guide cable. The video processor 5 is to perform signal processing for an image pickup signal from the CCD of the endoscope 2 and to supply image data (endoscope live image data, for example) on the basis of the image pickup signal to the monitor 6. The monitor 6 is connected to the video processor 5 by a connection cable 5A. The monitor 6 displays an endoscope image on the basis of image data from the video processor 5.

In the endoscope system 1 of this embodiment, a balloon 9 for fixation is mounted at a tip-end outer circumference portion of the insertion portion 2B of the endoscope 2. To this balloon 9, an air supply tube 10 provided along the insertion portion 2B from the base end side to the tip end side of the insertion portion 2B is connected. The base end portion of the air supply tube 10 on the operation portion 2A side is connected to a connector 2a provided at a lower part of the operation portion 2A. To this connector 2a, a connector 13A provided at one end of a tube for supplying air to an endoscope balloon (hereinafter referred to as a first air-supply tube) 13 having the other end connected to an endoscope balloon control device 7, which will be described later, is connected. By this, the balloon 9 is inflated by air supply from the endoscope balloon control device 7 to be temporarily fixed to a digestive tract such as an intestinal tract.

The overtube 3 is to guide the insertion portion 2B by inserting the endoscope 2 to be inserted into the digestive tract, for example, and has an inner diameter slightly larger than the outer diameter of the insertion portion 2B of the endoscope. Also, this overtube 3 is configured to have flexibility similarly to the insertion portion 2B of the endoscope 2. Moreover, at the tip-end outer circumference portion of this overtube 3, a balloon 11 for tube fixation is mounted.

To the balloon 11, an air supply tube 12 provided from the base end side to the tip end side of the overtube 3 is connected. The base end portion of the air supply tube 12 opposite to the balloon 11 side (insertion port side to insert the endoscope 2 of the overtube 3) is connected to a connector 3a provided in the vicinity of the insertion port of the overtube 3. To this connector 3a, a connector 14A provided at the one end of a tube for supplying air to the overtube balloon (hereinafter referred to as a second air-supply tube) 14 having the other end connected to the endoscope balloon control device 7 is connected. By this, the balloon 11 is inflated by air supply from the endoscope balloon control device 7 to be temporarily fixed to a digestive tract such as an intestinal tract.

The endoscope balloon control device 7 is to control various operations such as air-supply flow rates of the balloon 9 of the endoscope 2 and the balloon 11 of the overtube 3.

Figure 2:
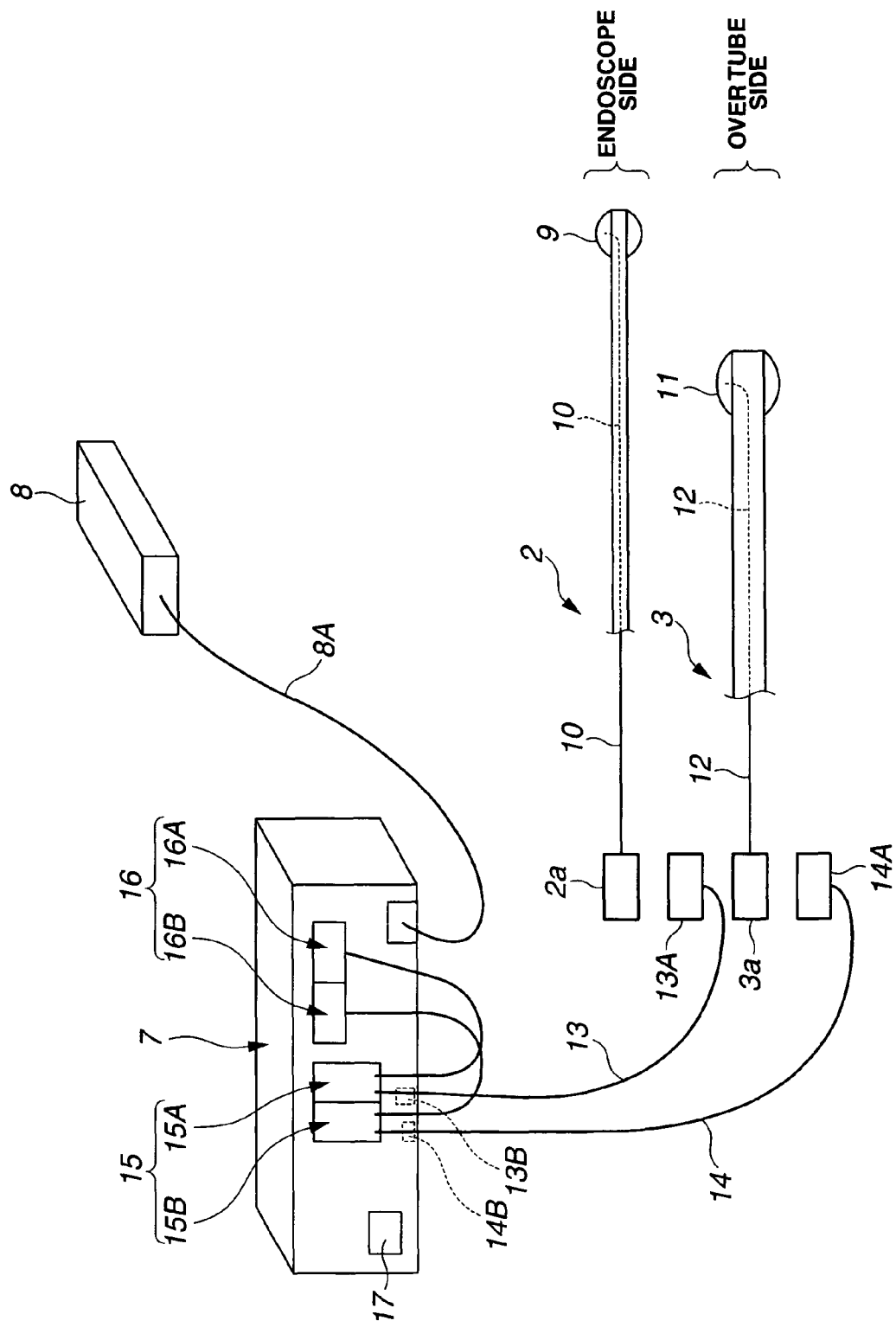
FIG. 2 is a configuration diagram showing an outline configuration of the endoscope balloon control device in FIG. 1.

FIG. 2 is a configuration diagram showing a schematic configuration of the endoscope balloon control device. As shown in FIG. 2, the endoscope balloon control device 7 is provided with a tank 15 for preventing counter flow and a pressure indicator 16 and a power switch 17 on the front. The tank 15 for preventing counter flow is configured capable of preventing counter flow of a liquid and has a tank 15A for the balloon 9 of the endoscope 2 and a tank 15B for the balloon 11 of the overtube 3. To these tanks 15A, 15B, the corresponding first and the second air-supply tubes 13, 14 are connected, respectively.

The tanks 15A, 15B supply air to each of the balloons 9, 11 through the first and the second air-supply tubes 13, 14 by increasing the internal pressure through a first and a second pumps 32a, 32b (See FIG. 4), which will be described later, by control of the endoscope balloon control device 7. In this case, the tanks 15A, 15B prevent counter flow of the liquid from the first and the second air-supply tubes 13, 14 by counter-flow preventing mechanisms, not shown.

In this way, in the endoscope balloon control device 7 of this embodiment comprises an air-supply pipeline through the air-supply tube 10 connected to the balloon 9 of the endoscope 2, the first air-supply tube 13 and the tank 15A and an air-supply pipeline through the air-supply tube 12 connected to the balloon 11 of the overtube 3, the second air-supply tube 14 and the tank 15B.

Also, the pressure indicator 16 indicates a pressure value of the pipelines connected to the balloons 9, 11 using detectors (not shown). This pressure indicator 16 has an indicator 16A for the balloon 9 of the endoscope 2 and an indicator 16B for the balloon 11 of the overtube 3. The indicator 16A indicates a pressure value in the pipeline for the balloon 9 of the endoscope 2, while the indicator 16B indicates a pressure value in the pipeline for the balloon 11 of the overtube 3. The power switch 17 is a switch for switching between a power on state and an off state of the endoscope balloon control device 7.

Also, as shown in FIGS. 1 and 2, a remote controller 8 is connected to one face of the endoscope balloon control device 7 through a connection cable 8A. This remote controller 8 is electrically connected to a control portion 35 provided inside the endoscope balloon control device 7, as will be described later, through the connection cable 8A.

In this embodiment, the endoscope balloon control device 7 is supplied with an operation signal for pressure control and air-supply amount control of the respective balloons 9, 11 through an operation of the remote controller 8 by an operator during an operation.

Figure 3A:
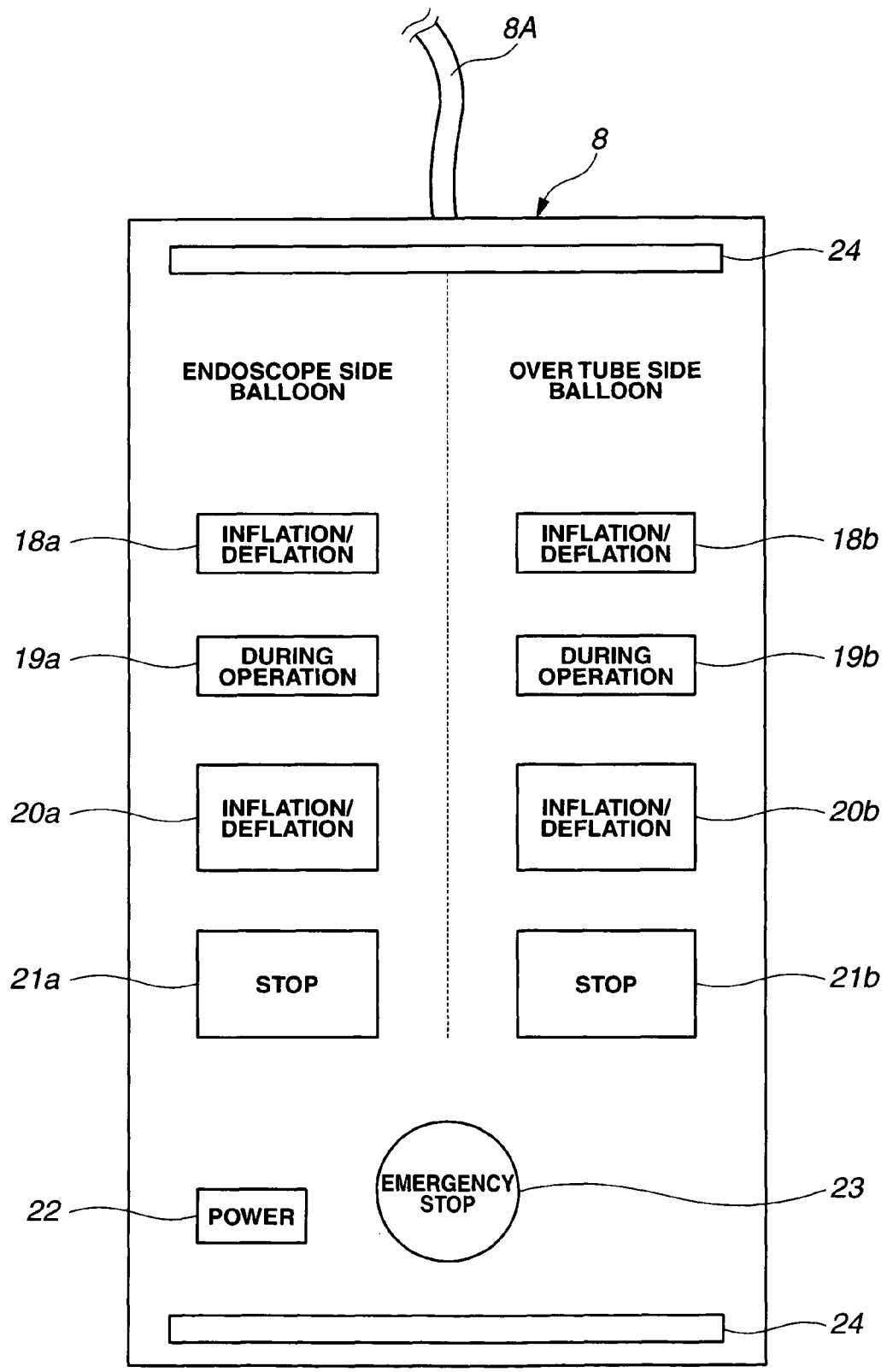
FIG. 3A is a front view showing a configuration example of a remote controller in FIG. 2.
Figure 3B:
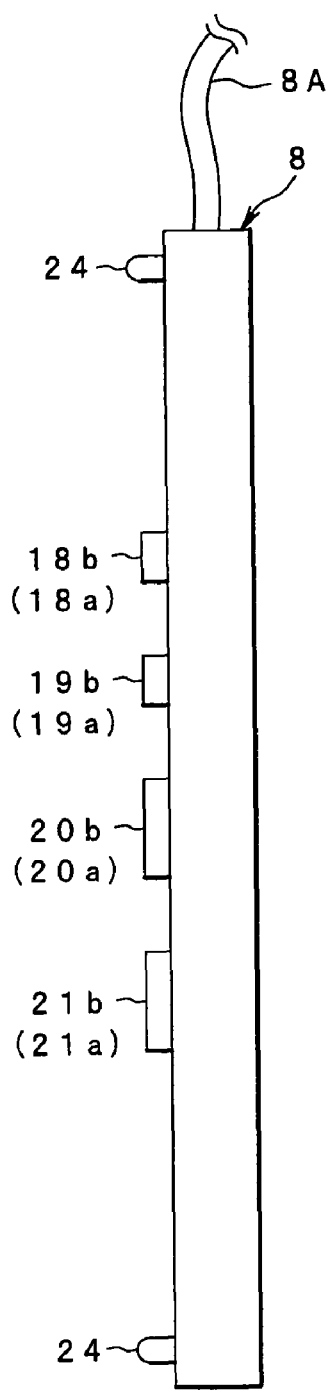
FIG. 3B is a side view showing a configuration example of a remote controller in FIG. 2.

FIGS. 3A and 3B are for explaining a configuration example of the remote controller 8, in which FIG. 3A is a top view and FIG. 3B is a side view.

As shown in FIG. 3A, the remote controller 8 has balloon inflation/deflation display portions 18a, 18b and balloon during operation display portions 19a, 19b as display means for having the operator recognize the state of the balloon 9 of the endoscope 2 and the balloon 11 of the overtube 3. The balloon inflation/deflation display portions 18a and the balloon during operation display portions 19a are for display of the balloon 9 on the endoscope side, while the balloon inflation/deflation display portions 18b and the balloon during operation display portions 19b are for display of the balloon 11 on the overtube side. These balloon inflation/deflation display portions 18a, 18b and balloon during operation display portions 19a, 19b are disposed in the right and left on the remote controller main body, for example, so that the operator can easily discriminate between the balloon for endoscope side and the balloon for the overtube side.

Moreover, on the remote controller 8, various buttons for endoscope side balloon control and the various buttons for the overtube side balloon control are disposed in the right and left on the remote controller main body, for example, so that the operator can operate easily. On the left side of the remote controller 8, the balloon inflation/deflation display portions 18a and the balloon during operation display portions 19a as display means for the endoscope side balloon and an inflation/deflation button 20a and a stop button 21a as operation buttons for the endoscope side balloon control are provided.

On the right side of the remote controller 8, the balloon inflation/deflation display portions 18b and the balloon during operation display portions 19b as display means for the overtube side balloon and an inflation/deflation button 20b and a stop button 21b as operation buttons for the overtube side balloon control are provided. Moreover, at a lower part of the remote controller 8, a power button 22 and an emergency stop button 23 are provided.

The balloon inflation/deflation display portion 18a displays the inflation state or the deflation state of the balloon 9 of the endoscope 2 at driving control on the basis of the operation of the inflation/deflation button 20a or the stop button 21a by the operator. Also, the balloon inflation/deflation display portion 18a performs lighted display at the inflation state and non-lighted display at the deflation state so that the display at the inflation state and the display at the deflation state can be distinguished, for example.

The balloon during operation display portion 19a is to have the operator recognize that the balloon 9 of the endoscope 2 is during operation such as inflation or deflation through display. The inflation/deflation button 20a is a button to instruct start of air-supply/suction with respect to the balloon 9 of the endoscope 2. Inflation is performed by pressing down after power on, deflation by the subsequent pressing and inflation/deflation of the balloon 9 is alternated at each pressing of the switch. The stop button 21a instructs pressure keeping of the pipeline in the balloon 9 of the endoscope 2 so that the state of the balloon 9 is maintained.

On the other hand, the balloon inflation/deflation display portion 18b displays the inflation state or the deflation state of the balloon 11 of the overtube 3 at driving control on the basis of the operation of inflation/deflation button 20b or the stop button 21b by the operator. Also, the balloon inflation/deflation display portion 18b performs lighted display at the inflation state and non-lighted display at the deflation state so that the display at the inflation state and the display at the deflation state can be distinguished, for example.

The balloon during operation display portion 19b is to have the operator recognize that the balloon 11 of the overtube 3 is during operation such as inflation or deflation through display.

The inflation/deflation button 20b is a button to instruct start of air-supply/suction into the balloon 11 of the overtube 3. Inflation is performed by pressing down after power on, deflation by the subsequent pressing and inflation/deflation of the balloon 11 is alternated by each pressing of the switch. The stop button 21b instructs pressure keeping of the pipeline in the balloon 11 of the overtube 3 so that the state of the balloon 11 is maintained.

Also, the power button 22 is a button for switching the power supply of the endoscope balloon control device 7 between the on state or the off state. The emergency stop button 23 is a button for emergency stop of air-supply control or the like of the respective balloons 9, 11 by the endoscope balloon control device 7 by directly turning off a first to a third breakers 31a to 31c, which will be described later, of the endoscope balloon control device 7.

In this embodiment, as shown in FIG. 3A, projection portions 24 for preventing erroneous operation are provided at an upper part and a lower part on the operation surface of the remote controller 8. These projection portions 24 are provided so that they are higher than the height of the various buttons such as inflation start buttons 20a, 20b and deflation start buttons 21a, 21b as shown in FIG. 3B. By this, even if the operator drops the remote controller 8 by mistake, erroneous operation of the various buttons such as the inflation start buttons 20a, 20b and the deflation start buttons 21a, 21b can be prevented by the projection portions 24.

In this embodiment, the balloon inflation/deflation display portions 18a, 18b and the balloon during operation display portions 19a, 19b are configured using LED, for example. Not limited to this, the balloon inflation/deflation display portions 18a, 18b and the balloon during operation display portions 19a, 19b may be configured using other display means only if they have the operator recognize the state of the balloons 9, 11.

For example, the balloon inflation/deflation display portions 18a, 18b and the balloon during operation display portions 19a, 19b may be displayed in different colors according to the state. Alternatively, the balloon inflation/deflation display portions 18a, 18b and the balloon during operation display portions 19a, 19b may be displayed by providing them in a liquid crystal screen configured by a liquid crystal or the like. Moreover, in this case, the balloon inflation/deflation display portions 18a, 18b and the balloon during operation display portions 19a, 19b may be displayed using patterns such as icons. Also, the balloon inflation/deflation display portions 18a, 18b and the balloon during operation display portions 19a, 19b may be provided on the front surface of the endoscope balloon control device 7, not only on the remote controller 8.

Figure 4:
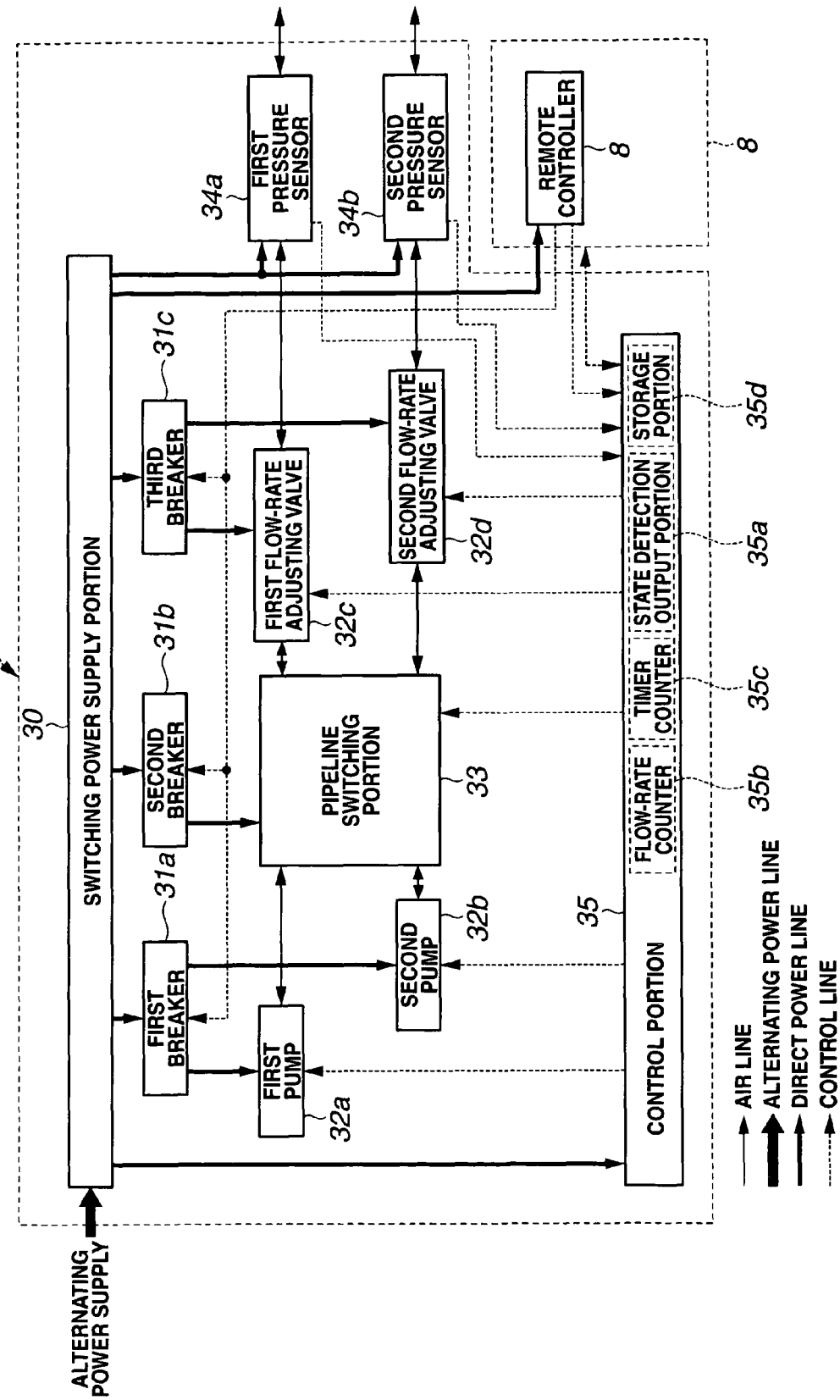
FIG. 4 is a block diagram showing an internal configuration of the endoscope balloon control device in FIG. 2.

Next, the internal configuration of the endoscope balloon control device 7 will be described referring to FIG. 4. FIG. 4 is a block diagram showing the internal configuration of the endoscope balloon control device.

As shown in FIG. 4, the endoscope balloon control device 7 has a switching power supply portion 30, the first to the third breakers 31a to 31c, a first and a second pumps 32a, 32b, a first and a second flow-rate adjusting valves 32c, 32d, a pipeline switching portion 33, a first and a second pressure sensors 34a, 34b, and a control portion (control unit) 35, which is the control means.

To the switching power supply portion 30, an alternating power supply is supplied from an external commercial power supply portion through a connection cord, not shown. The switching power supply portion 30 converts the supplied alternating power supply to a direct power supply and supplies it to the first to the third breakers 31a to 31c, the control portion 35 and the remote controller 8.

The first breaker 31a is electrically connected to the first and the second pumps 32a, 32b and the emergency stop button 23 of the remote controller 8. The first breaker 31a supplies the direct power supply to the first and the second pumps 32a, 32b and stops the supply of the direct power supply to the first and the second pumps 32a, 32b when an operation signal is supplied from the emergency stop button 23.

The second breaker 31b is electrically connected to the pipeline switching portion 33 and the emergency stop button 23 of the remote controller 8. The second breaker 31b supplies the direct power supply to the pipeline switching portion 33 and stops the supply of the direct power supply to the pipeline switching portion 33 when the operation signal from the emergency stop button 23 is supplied.

The third breaker 31c is electrically connected to the first and the second flow-rate adjusting valves 32c, 32d and the emergency stop button 23 of the remote controller 8. The third breaker 31c supplies the direct power supply to the first and the second flow-rate adjusting valves 32c, 32d and stops the supply of the direct power supply to the first and the second flow-rate adjusting valves 32c, 32d when the operation signal from the emergency stop button 23 is supplied.

The first and the second pumps 32a, 32b are connected to the input side of the pipeline switching portion 33 through an air lines, respectively. Also, the first and the second pumps 32a, 32b are driven/controlled on the basis of the control signal from the control potion 35.

To the output side of the pipeline switching portion 33, the first and the second flow-rate adjusting valves 32c, 32d are connected through the air lines, respectively. The first and the second flow-rate adjusting valves 32c, 32d are valves in which opening/closing can be adjusted by the control portion 35 and capable of flow-rate adjustment of air outputted on the basis of a control signal from the control portion 35.

The first and the second pressure sensors 34a, 34b measure pressures of the pipelines connected to the first and the second flow-rate adjusting valves 32c, 32d. In this embodiment, the measurement results by the first and the second pressure sensors 34a, 34b are supplied to the control portion 35, and the control portion 35 is configured so that the first and the second pumps 32a, 32b, the pipeline switching portion 33, the first flow-rate adjusting valve 32c, the second flow-rate adjusting valve 32d are controlled to have a desired air pressure on the basis of the supplied measurement results. The first and the second pressure sensors 34a, 34b are connected to the first and the second air-supply tubes 13, 14 through the air-supply line, the connectors 7A, 7B, 13B and 14B.

In this way, the endoscope balloon control device 7 has an air-supply pipeline comprising the first pump 32a, the first flow-rate adjusting valve 32c through the pipeline switching portion 33 and the first pressure sensor 34a, and an air-supply pipeline comprising the second pump 32b, the second flow-rate adjusting valve 32d through the pipeline switching portion 33 and the second pressure sensor 34b.

Figure 27:
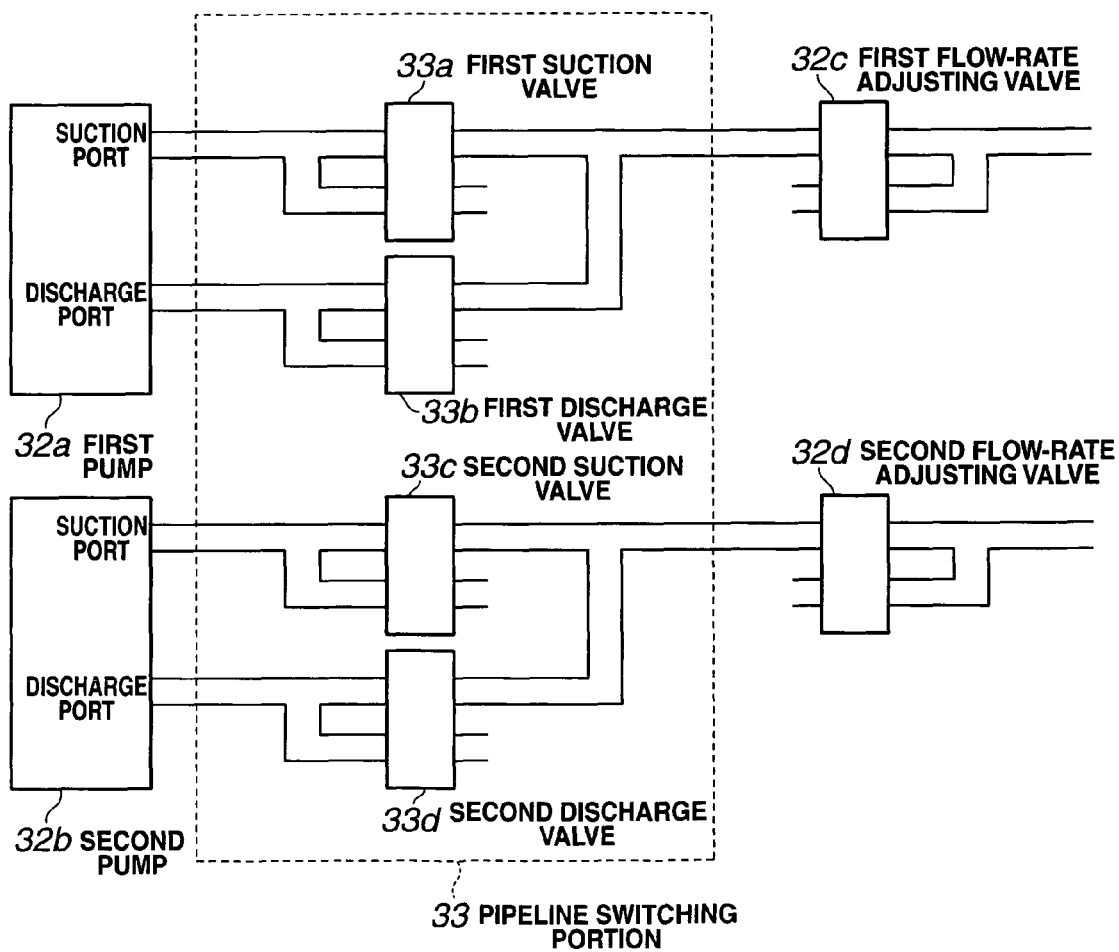
FIG. 27 is a block diagram showing a pipeline switching portion in the block diagram showing the internal configuration of the endoscope balloon control device in FIG. 4.

Also, the pipeline switching portion 33 is capable of switching the pipelines provided inside so that the pipeline state according to an execution mode inside the endoscope balloon control device 7 can be obtained. As the execution mode, for example, four execution modes of an air-supply mode, a suction mode, a maintained mode and an open mode are realized using the pipeline system as shown in FIG. 27.

A first suction valve 33a, a first discharge valve 33b, a second suction valve 33c, a second discharge valve 33d, the first flow-rate adjusting valve 32c, the second flow-rate adjusting valve 32d are valves to turn on the path only in vertical one direction.

In order to have the pipeline of the first pump 32a in the air-supply state, the first suction valve 33a, the first discharge valve 33b, the first flow-rate adjusting valve 32c are turned on in the lower, upper, upper paths, respectively.

In order to have the pipeline of the first pump 32a in the suction state, the first suction valve 33a, the first discharge valve 33b, the first flow-rate adjusting valve 32c are turned on in the upper, lower, upper paths, respectively.

In order to have the pipeline of the first pump 32a in the maintained state, the first suction valve 33a, the first discharge valve 33b, the first flow-rate adjusting valve 32c are turned on in the lower, lower, upper paths, respectively.

In order to have the pipeline of the first pump 32a in the open state, the first suction valve 33a, the first discharge valve 33b, the first flow-rate adjusting valve 32c are turned on in the lower, lower, lower paths, respectively.

By setting the valves in the pipeline of the second pump 32b, the similar pipeline states are realized.

This switching is controlled on the basis of the control signal from the control portion 35. As a result, the pipeline on the balloon 9 side of the endoscope 2 connected to the rear stage side and the pipeline on the balloon 11 side of the overtube 3 side can be brought into the pipeline states on the basis of the desired execution modes, respectively. The control portion 35 is to control the entire endoscope balloon control device 7 and has a state detection output portion 35a, a flow rate counter 35b, a timer counter 35c and a storage portion 35d therein, which are the state detecting means and the state information output means.

The state detection output portion 35a detects the operating state of the balloon 9 or the balloon 11 from the states of the first and the second pumps 32a, 32b, the pipeline switching portion 33, the first and the second flow-rate adjusting valves 32c, 32d and the first and the second pressure sensors 34a, 34b and outputs the state information to control display of the balloon inflation/deflation display portions 18a, 18b and the balloon during operation display portions 19a, 19b of the remote controller 8 on the basis of this detection result. That is, the control portion 35 controls display of the balloon inflation/deflation display portions 18a, 18b and the balloon during operation display portions 19a, 19b of the remote controller 8 on the basis of the state information detected by the state detection output portion 35a.

The flow rate counter 35b is the flow-rate detecting means for counting an air-supply/suction flow rate to the balloon 9 of the endoscope 2 and the balloon 11 of the overtube 3. Also, the timer counter 35c is a timer counter for counting air-supply time, suction time and the like of the respective balloons 9, 11 and has a timer for measuring a predetermined time.

The storage portion 35d stores a main program and programs on the basis of various modules, which will be described later.

The control portion 35 controls the first and the second pumps 32a, 32b, the pipeline switching portion 33 and the first and the second flow-rate adjusting valves 32c, 32d using the flow rate counter and the timer counter by executing the programs on the basis of the operation signals from the remote controller 8.

In this way, the endoscope balloon control device 7 can measure the air supply time, suction time, air-supply flow rate time and the like to the balloon 9 of the endoscope 2 and the balloon 11 of the overtube 3 and by using these measurement results, it can control the air-supply/suction flow rates to the balloon 9 of the endoscope 2 and the balloon 11 of the overtube 3.

Also, in this embodiment, by control by the control portion 35, the endoscope balloon control device 7 can make the balloon inflation/deflation display portions 18a, 18b and the balloon during operation display portions 19a, 19b of the remote controller 8 display the operating state of the respective balloons 9, 11.

Next, a basic operating state of the endoscope system 1 will be described referring to FIGS. 5 to 11.

Figure 5:
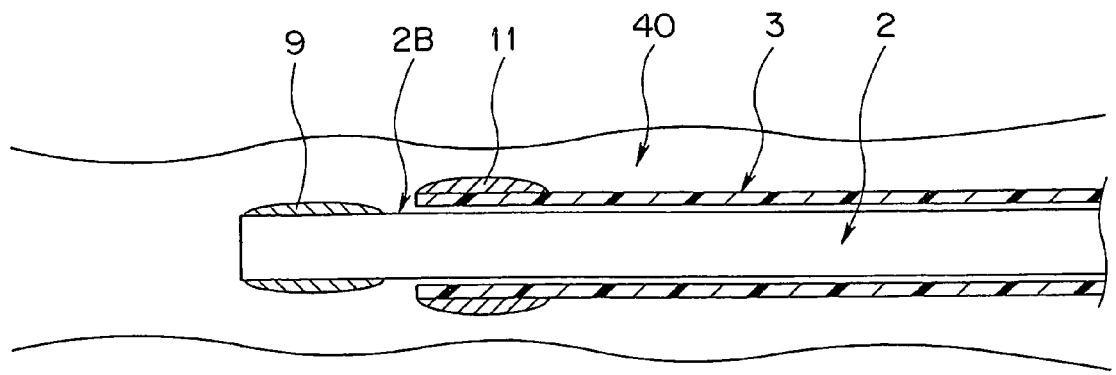
FIGS. 5 to 11 are for explaining an operation state of the endoscope and an overtube using each balloon and FIG. 5 is an explanatory view showing a state where each balloon is deflated and the endoscope is inserted into the overtube and inserted into a digestive tract.
Figure 6:
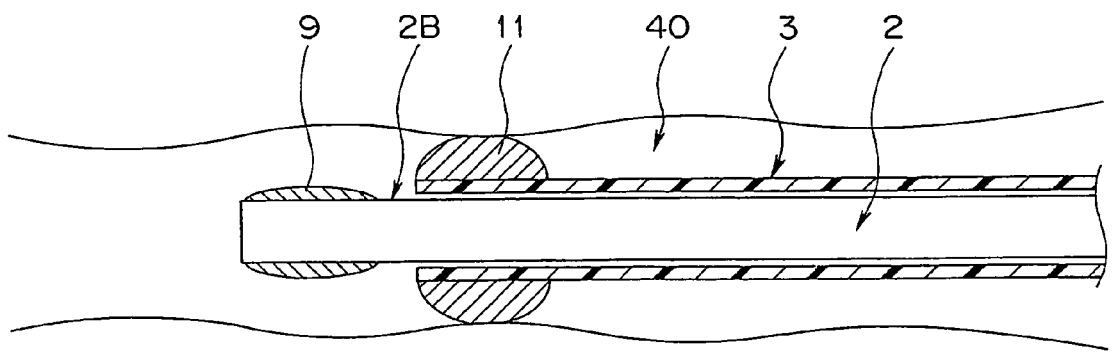
Figure 7:
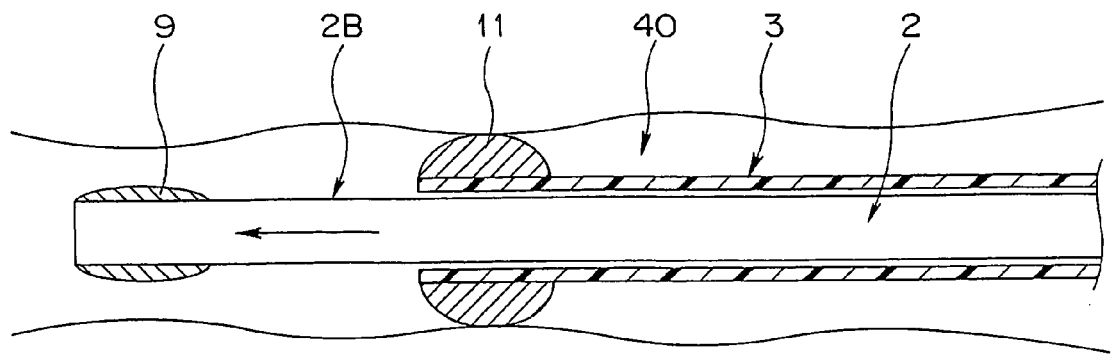
Figure 8:
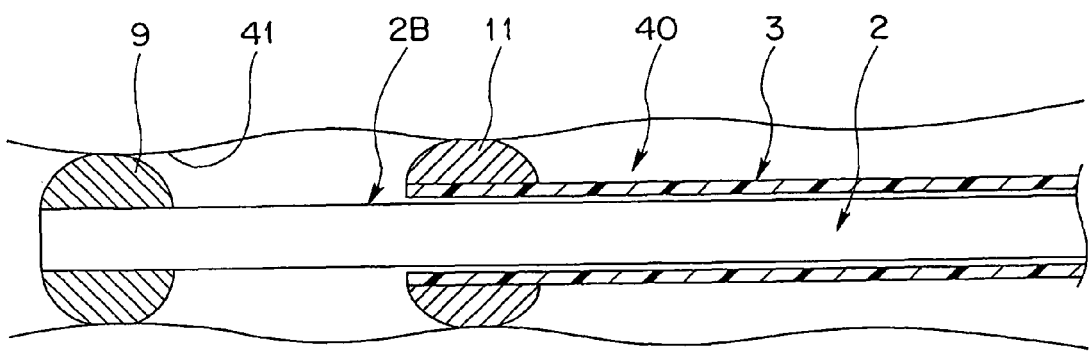
Figure 9:
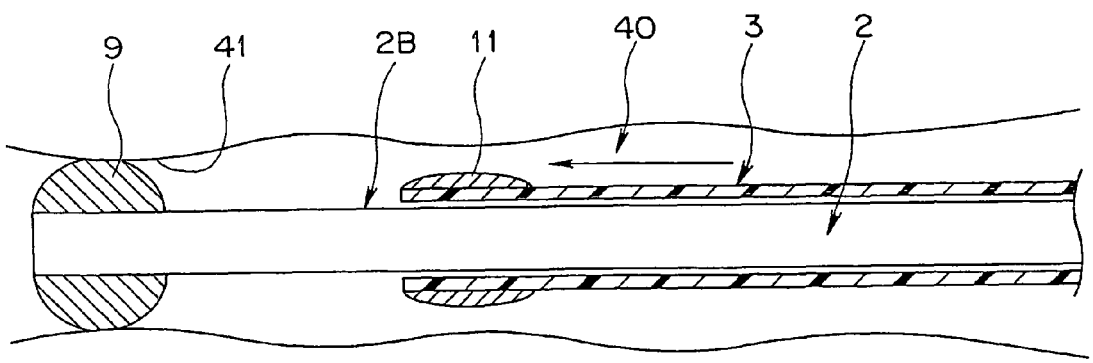
Figure 10:
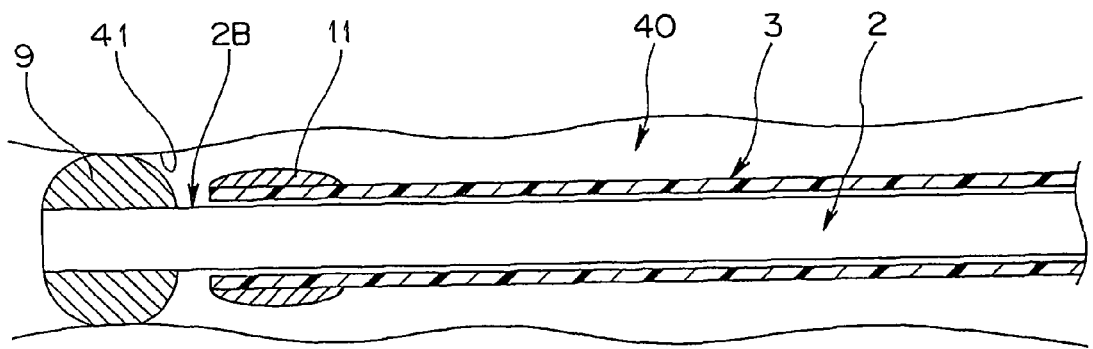
Figure 11:
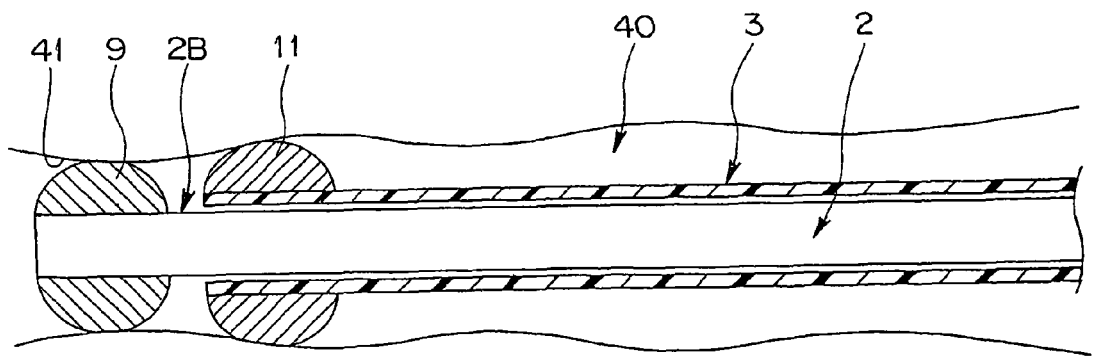

FIGS. 5 to 11 are explanatory views for explaining the operating states of the endoscope and the overtube using the balloon of the endoscope 2 and the balloon of the overtube. FIG. 5 shows a state where the respective balloons are deflated and the endoscope is inserted through the overtube and inserted into the intestinal tract, FIG. 6 shows a state where the balloon of the overtube is inflated and fixed to the intestinal tract, FIG. 7 shows a state where the endoscope is further inserted into the overtube from the state in FIG. 6, FIG. 8 shows a state where the balloon of the endoscope is inflated in the state in FIG. 7 and fixed to the intestinal wall, FIG. 9 shows a state where the balloon of the overtube is deflated in the state in FIG. 8 and the overtube is further inserted, FIG. 10 shows a state where the tip end of the overtube is moved to the tip end portion of the endoscope from the state in FIG. 9, and FIG. 11 shows a state where the balloon of the overtube is inflated in the state in FIG. 10 and fixed to the intestinal wall, respectively.

As shown in FIG. 5, the operator inserts the endoscope 2 into the overtube 3. In this case, the balloon 9 of the endoscope 2 and the balloon 11 of the overtube 3 are drained of air and deflated, and the operator starts insertion of the endoscope 2 into a subject in this state.

Next, when the operator inserts the tip ends of the endoscope 2 and the overtube 3 to duodenum descending limb, for example, the inflation/deflation button 20b (see FIG. 3) on the overtube side of the remote controller 8 is pressed down as shown in FIG. 6 so as to supply air from the second pump 32b to the balloon 11 for fixing the main body mounted at the tip end of the overtube 3, and this balloon 11 is inflated and the overtube 3 is fixed to an intestinal tract 40. Next, the operator maintains the overtube 3 at the intestinal tract 40 and inserts only the insertion portion 2B of the endoscope 2 to the deep portion as shown in FIG. 7.

And the operator presses down the inflation/deflation button 20a (See FIG. 3) on the endoscope side of the remote controller 8 in the state where the insertion portion 2B of the endoscope 2 is inserted by a predetermined distance as shown in FIG. 8 so as to supply air from the first pump 32a into the balloon 9 for fixing the main body mounted at the tip end of the endoscope 2 so that the balloon 9 is inflated and fixed to the intestinal tract 41.

Next, the operator presses the inflation/deflation button 20b (See FIG. 3) on the overtube side of the remote controller 8 so as to release air in the balloon 11 by the pipeline switching portion 33 and to suction air in the balloon 11 of the overtube 3 from the second pump 32b to deflate the balloon 11 (See FIG. 9).

Then, the operator inserts the overtube 3 to the deep portion along the endoscope 2 as shown in FIG. 9 and inserts the tip end of the overtube 3 close to the tip end of the insertion portion 2B of the endoscope 2.

And the operator presses down the inflation/deflation button 20b (See FIG. 3) on the overtube side of the remote controller 8 in the state where the tip end of the overtube 3 is inserted close to the tip end of the insertion portion 2B as shown in FIG. 11, and air is supplied from the second pump 32b to the balloon 11 of the overtube 3 to inflate this balloon 11 and fix the overtube 3 to the intestinal wall 41.

Also, the operator presses down the inflation/deflation button 20a (See FIG. 3) on the endoscope side of the remote controller 8 to release air in the balloon 9 by the pipeline switching portion 33 and suction the air in the balloon 9 of the endoscope 2 from the first pump 32a so as to deflate the balloon 9, and the insertion portion 2B is further inserted to the deep portion.

By repeating the above operation from FIG. 5 to FIG. 11, the endoscope 2 and the overtube 3 are further inserted to the deep portion so that the insertion portion 2B of the endoscope 2 can be inserted to a desired position.

Next, action of the endoscope balloon control device of this embodiment will be described referring to FIG. 12.

Figure 12:
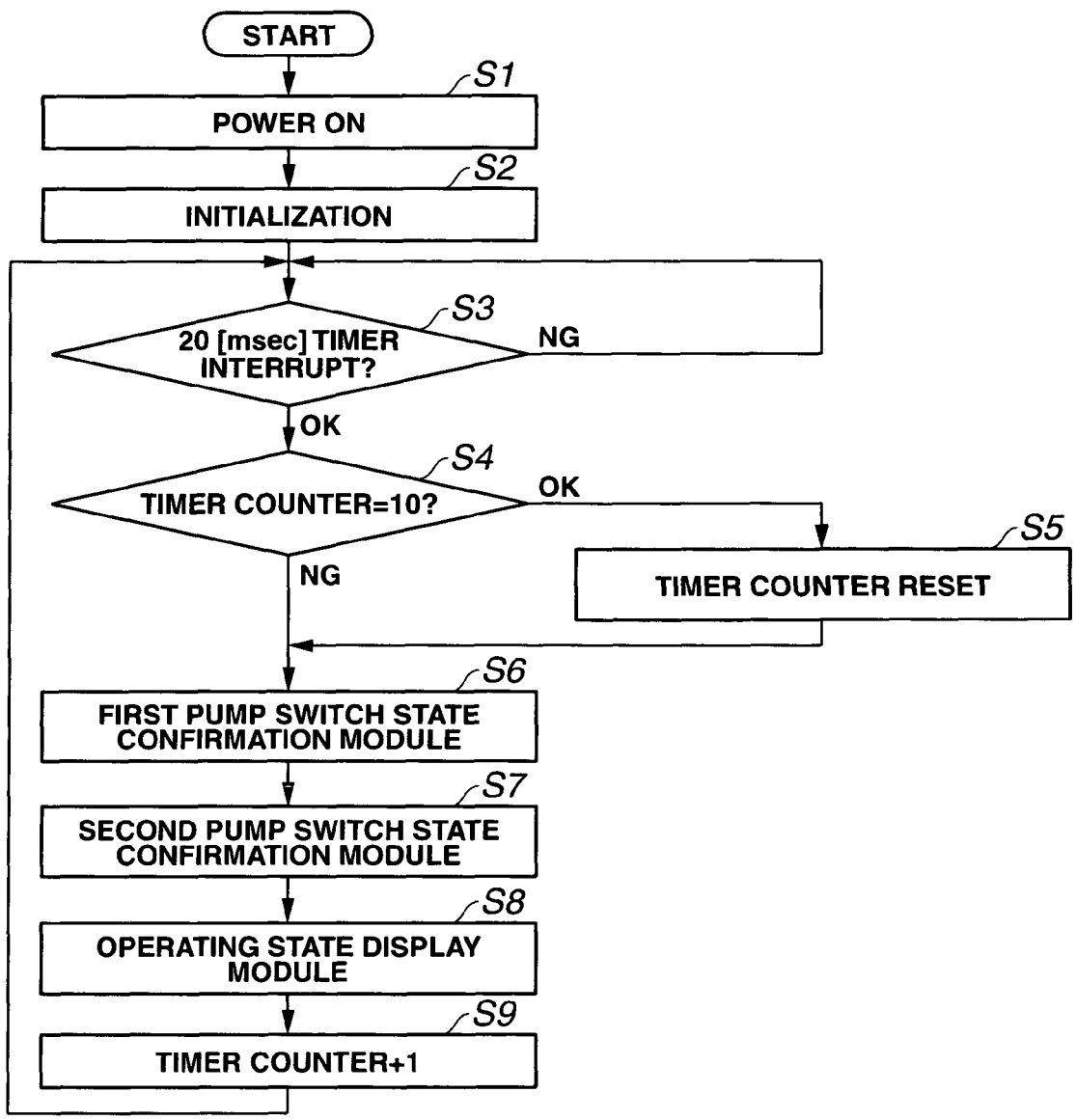
FIG. 12 is a flowchart showing a main program of a control portion for explaining action of an endoscope balloon control device.

FIG. 12 is for explaining the action of the endoscope balloon control device and is a flowchart showing a main program of the control portion. Suppose that the operator uses the endoscope system 1 in FIG. 1 to perform an endoscopic inspection inside a digestive tract. When the operator presses down the power button 22 of the remote controller 8 shown in FIG. 3 (or the power switch 17 shown in FIG. 2), the control portion 35 reads the main program shown in FIG. 12 from the storage portion inside thereof, not shown, and starts the main program.

The control portion 35 confirms the power ON state at the processing of Step S1 and initializes various devices in the endoscope balloon control device 7 at the processing of Step S2. As this initialization, the control portion 35 starts the first and the second pumps 32a, 32b and opens the pipeline by the pipeline switching portion 33. Also, the control portion 35 resets and initializes the timer counter 9 and the like, not shown, in the control portion 35.

And the control portion 35 determines 20 msec timer interrupt at the determination processing of the subsequent Step S3 and if it is determined that there was an interrupt, the processing goes to Step S4, while if it is determined that there was no interrupt, the determination processing is continued.

As the timer, such a timer that measures 20 msec is used to operate the processing routine shown in FIG. 12 at every 20 msec.

And the control portion 35 determines if a counter value of the timer counter for counting 1 at every 20 msec of the timer is equal to 10 or not at the determining processing of Step S4, and if it is determined that the counter value is equal, the timer counter 9 is reset at the processing of Step S5 and the processing is moved to step S6. On the other hand, if it is determined that the counter value is not equal, the control portion 35 moves the processing to Step S6.

In this embodiment, the processing routine shown in FIG. 12 is carried out 10 times, that is, the balloon control is performed according to the operation of various buttons by the controller 8 of the operator by the time unit of 200 msec.

Next, the control portion 35 executes the first pump switch state confirmation module by the processing of Step S6, confirms the switch state of the remote controller 8 by this processing, takes in an operation signal and controls the pipeline switching portion 33 to have the pipelines state on the basis of this taken-in operation signal, and it also controls the operation for the first pump 32*a* on the basis of the operation signal.

And after completion of the processing based on the first pump switch state confirmation module of Step S6, the control portion 35 executes a second pump switch state confirmation module at the processing of Step S7, confirms the switch state of the remote controller 8 by this processing, takes in the operation signal and controls the pipeline switching portion 33 to have the pipeline state on the basis of this taken-in operation signal, and it also controls the operation for the second pump 32*b* on the basis of this operation signal.

After that, the control portion 35 executes the processing of the operation state display module at the processing of Step S8 and controls display of the balloon inflation/deflation display portions 18*a*, 18*b* and the balloon during operation display portions 19*a*, 19*b* of the remote controller 8 on the basis of the operation states of each block obtained by the processing of Step S2, Step S6 and Step S7 (including the operation states of the respective balloons 9, 11). Detection of the operation states is carried out by the state detection output portion 35*a* as mentioned above.

The display control example according to the inflation operation state of the balloons by the control portion 35 is shown in the following Table 1:

TABLE 1

|  |  | Balloon inflation/deflation display | Balloon during operation display | Pipeline state |
|---|---|---|---|---|
|  | Initial state | OFF | OFF | Open |
| Inflation | During inflation | ON | ON | Air supply |
|  | Inflation completed | ON | OFF | Maintained |
| Deflation | During deflation | OFF | ON | Suction |
|  | Deflation completed | OFF | OFF | Open |
|  | Emergency stop | OFF | OFF | Open |

Referring to the above Table 1, the balloon 9 of the endoscope 2 in this embodiment will be described. The control portion 35 controls display so that the balloon inflation/deflation display portion 18*a* and the balloon during operation display portion 19*a* are turned OFF when the operating state of the balloon 9 is in the initial state. The pipeline state in this case is an open state.

When the operating state of the balloon 9 is in the inflation state and during inflation, the control portion 35 turns on the balloon inflation/deflation display portion 18*a* and the balloon during operation display portion 19*a*. The pipeline state in this case is an air-supply state.

The control portion 35 turns on the balloon inflation/deflation display portion 18*a* when the operating state of the balloon 9 is in the inflation state and the inflation has been completed but it turns off the balloon during operation display portion 19*a*. The pipeline state in this case is a maintained state.

The control portion 35 turns off the balloon inflation/deflation display portion 18*a* and turns on the balloon during operation display portion 19*a* when the operating states of the balloons 9, 11 are in the deflated state and during deflation. The pipeline state in this case is a suction state.

The control portion 35 turns off the balloon inflation/deflation display portion 18*a* and the balloon during operation display portion 19*a* when the operating state of the balloon 9 is in the deflated state and deflation completed. The pipeline state in this case is in an open state.

Also, the control portion 35 turns off the balloon inflation/deflation display portion 18*a* and the balloon during operation display portion 19*a* when the operating state of the balloon 9 is in the emergency stop state by pressing down of the emergency stop button 23. The pipeline state in this case is the open state.

The display control by the control portion 35 is based on the operating state of the balloon 9 of the endoscope 2, but the balloon inflation/deflation display portion 18*b* and the balloon during operation display portion 19*b* of the overtube 3 are also controlled on the basis of the operating state of the balloon 11 of the overtube 3 as above. And the control portion 35 adds 1 to a counter value by the timer counter at the processing of Step S9 and returns the processing to the determination processing at Step S3 to continue processing repeatedly.

As mentioned above, according to this embodiment, by providing the state detection output portion 35*a* for detecting the operating states of the respective balloons 9, 11 and the balloon inflation/deflation display portions 18*a*, 18*b* and the balloon during operation display portions 19*a*, 19*b* which are display-controlled on the basis of the detection result by the state detection output portion 35*a*, the operating states of the respective balloons 9, 11 disposed in the digestive tract of the patient can be recognized by the operator. By this, insertion of the endoscope 2 and the overtube 3 into the deep portion can be carried out safely and rapidly, which can reduce pain of the patient.

Also, the endoscope balloon control device 7 can adjust an air-supply flow rate and a suction flow rate to the respective balloons 9, 11 by controlling opening/closing of the first flow-rate adjusting valve 32*c*, the second flow-rate adjusting valve 32*d*, and it can be adapted to balloon of various materials and various portions. Moreover, the endoscope balloon control device 7 measures the continuous air supply/suction time using the flow-rate counter 5*b*, and continuous air-supply operation or suction operation which might occur when the pipelines such as the first and the second air-supply tubes 13, 14 are removed, for example, can be prevented.

Also, the endoscope balloon control device 7 may perform control to open the pipeline upon detection that the maximum air-supply time, the maximum air-supply pressure and the maximum suction pressure are exceeded. It enables manipulation without application of a large force to the intestinal wall.

In this embodiment, the configuration where the remote controller 8 is connected to the endoscope balloon control device 7 has been described, but not limited to this, it may be constituted on the operation portion 2A of the endoscope 2 at the hand of the operator, or a foot switch for controlling the endoscope balloon control device 7 may be provided at the foot of the operator.

Also, the controller 8 may be so configured to transmit various remote controller operation signals using an infrared ray or radio frequency and to receive the infrared ray or radio frequency at a receiver portion provided at the endoscope balloon control device 7 so as to take in the remote controller signal. By this, operation by the operator is further facilitated.

Embodiment 2

Figure 13:
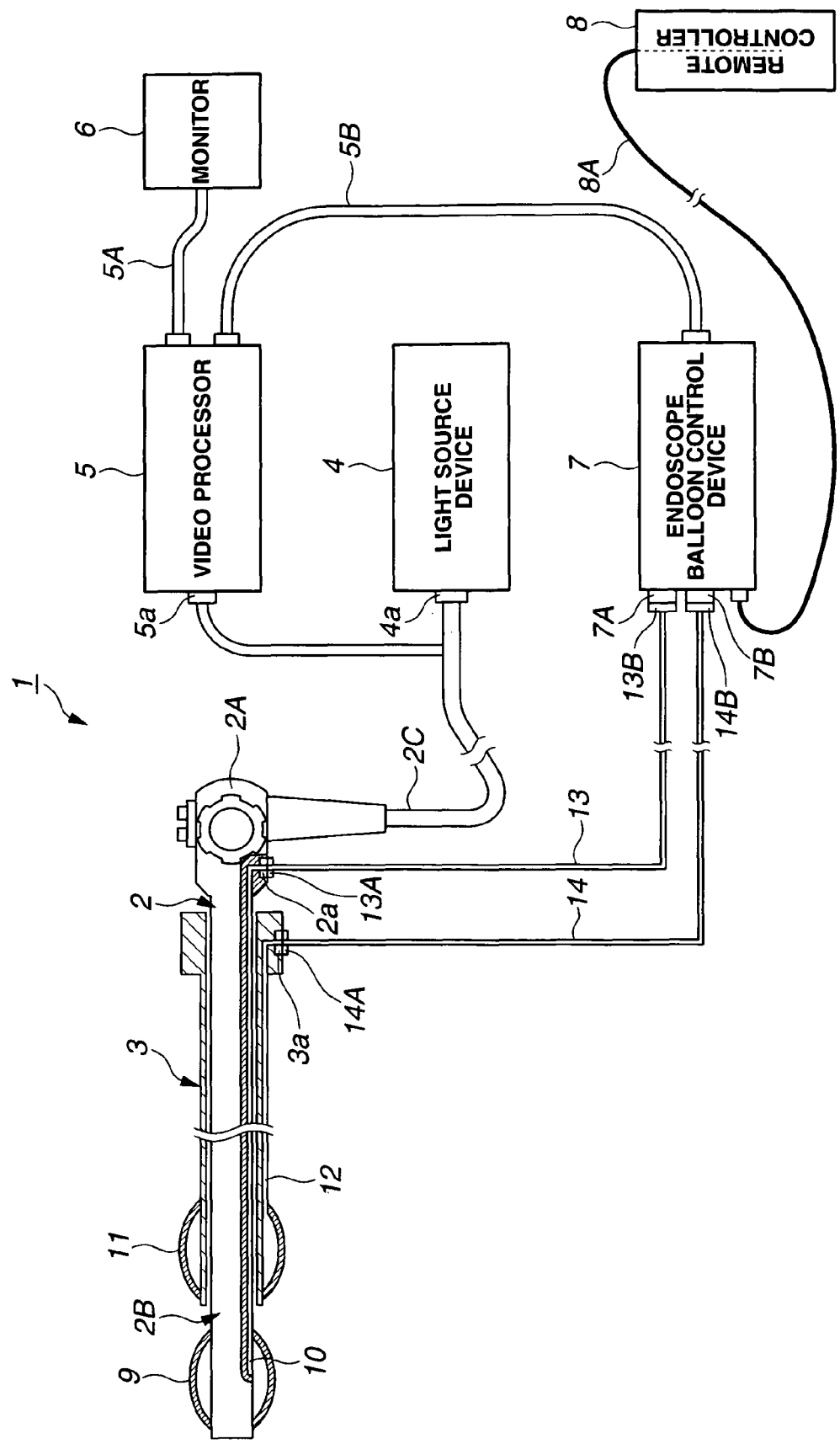
Figure 14:
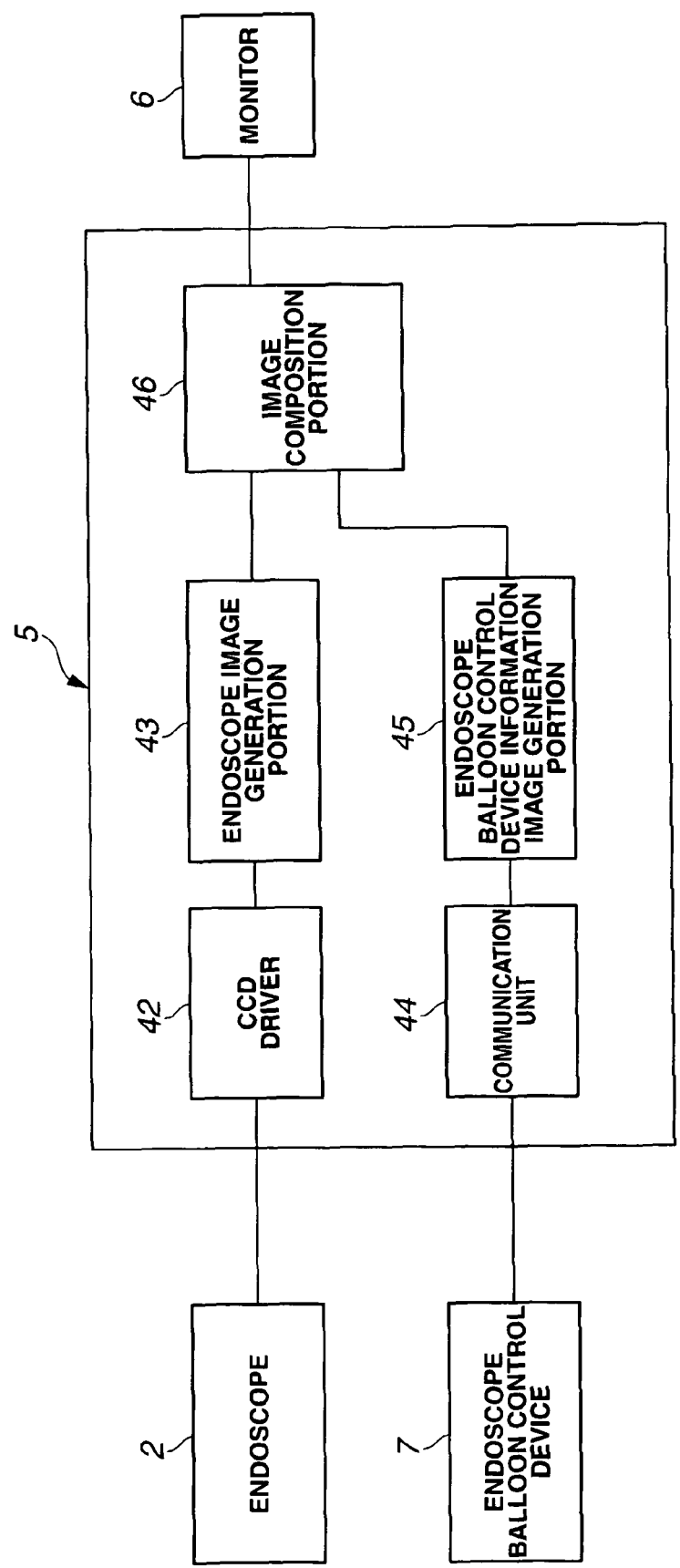
Figure 25:
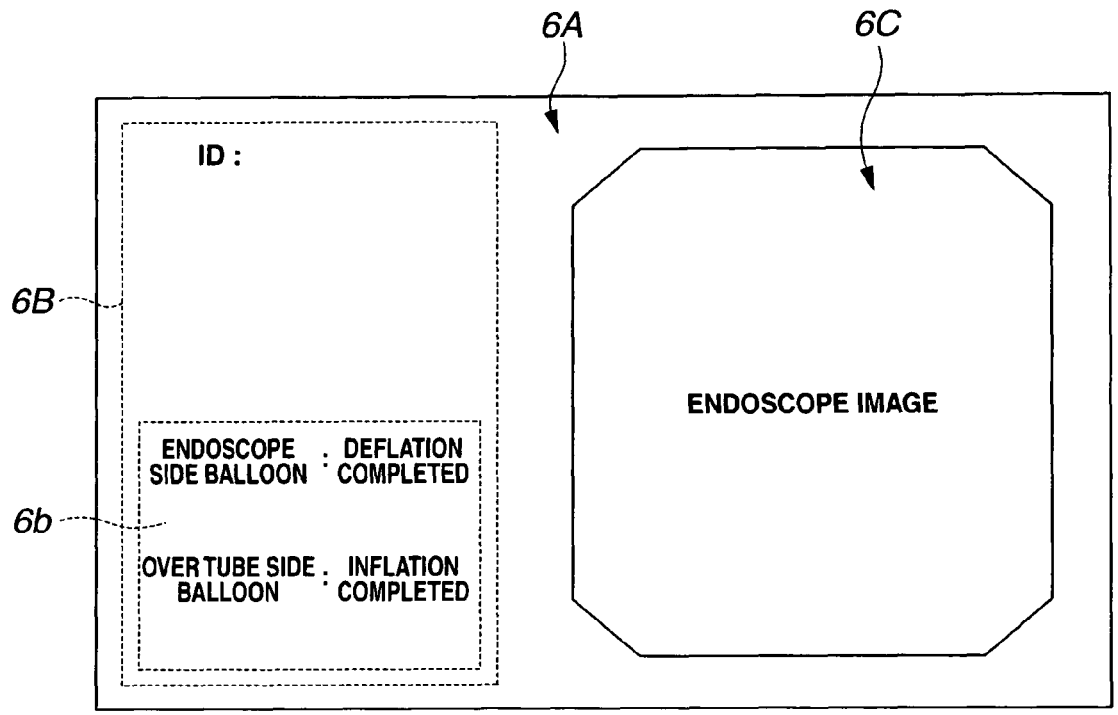
Figure 26:
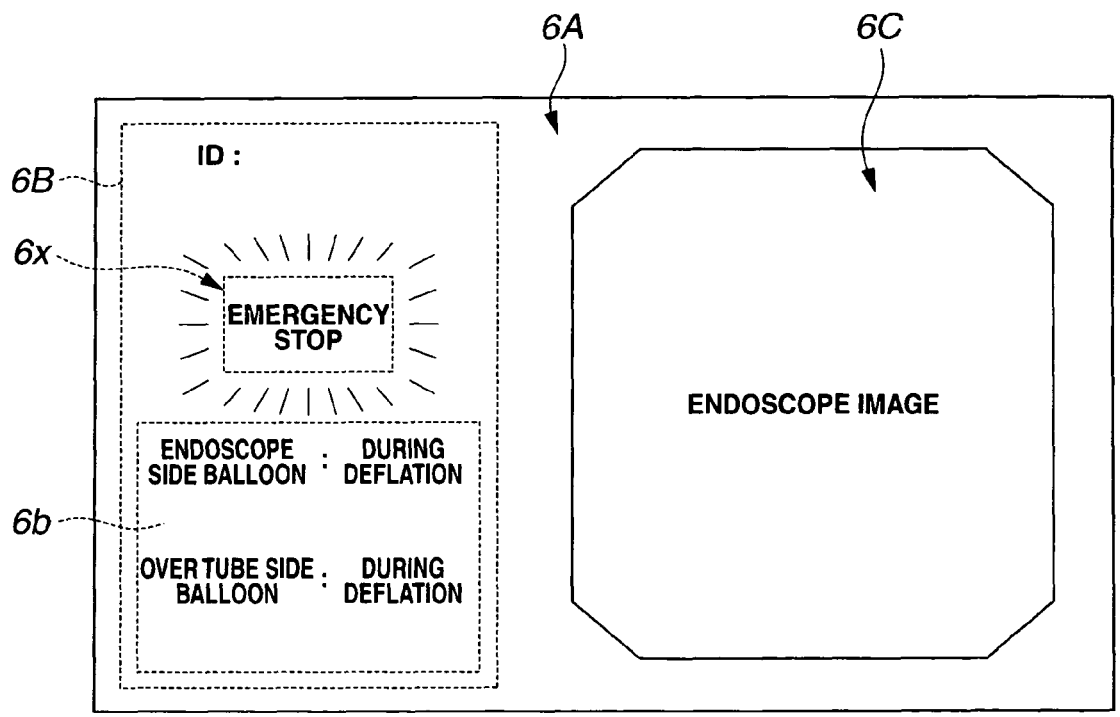

FIGS. 13 to 26 relate to a second embodiment of the present invention, in which FIG. 13 is a configuration diagram showing an entire configuration of the endoscope system to which the endoscope balloon control device is applied, FIG. 14 is a block diagram showing an internal configuration of the video processor 5 shown in FIG. 13, and FIGS. 15 to 26 are for explaining the display control operation by the endoscope balloon control device of this embodiment. FIGS. 15 to 25 are monitor screen display views corresponding to the operating state of the endoscope system and FIG. 26 is a monitor screen display view when the emergency stop button is pressed down, respectively.

As shown in FIG. 13, the endoscope balloon control device 7 of this embodiment is electrically connected to the video processor 5 of the endoscope system 1 of the above first embodiment through the connection cable 5B.

The endoscope balloon control device 7 supplies information such as operating states and the like of the respective balloons 9, 11 detected by the state detection output portion 35a to the video processor 5 through the connection cable 5B. The endoscope balloon control device 7 may be so configured that the information is sent using the infrared ray or radio frequency and the infrared or radio frequency is received by a receiver portion provided at the video processor 5 so as to take in the information.

The other configurations are the same as those of the first embodiment.

Next, the internal configuration of the video processor will be described referring to FIG. 14. As shown in FIG. 14, the video processor 5 has a CCD driver 42, an endoscope image generation portion 43, a communication unit 44, an endoscope balloon control device information image generation portion (hereinafter referred to as an endoscope balloon information image generation portion) 45 and an image composition portion 46.

The CCD driver 42 is electrically connected to a CCD (not shown) provided inside the tip end of the insertion portion 2B through the light source device 4, the universal cord 2C and a signal line, not shown, inside the endoscope 2. The CCD driver 42 is a driving circuit for driving the CCD (not shown) and takes in an image pickup signal obtained by driving the CCD and supplies it to the endoscope image generation portion 43. The endoscope image generation portion 43 applies signal processing to the image pickup signal from the CCD, generates image data on the basis of the image pickup signal (an endoscope live image data, for example) and supplies it to the image composition portion 46.

On the other hand, the communication unit 44 is electrically connected to the control portion 35 of the endoscope balloon control device 7 through the connection cable 5B. The communication unit 44 is capable of bidirectional communication with the control portion 35 of the endoscope balloon control device 7 and receives information such as the operating states and the like of the respective balloons 9, 11 detected by the state detection output portion 35a through communication with the control portion 35. And the communication unit 44 supplies the received and taken-in information to the endoscope balloon information image generation portion 45.

The endoscope balloon information image generation portion 45 generates an endoscope balloon information image on the basis of the information using saved character information, for example, on the basis of the supplied information and supplies it to the image composition portion 46. The image composition portion 46 composes the endoscope image from the endoscope image generation portion 43 and the endoscope balloon information image from the endoscope balloon information image generation portion 45 by superposition processing and outputs and displays a composed image signal obtained by composition on the monitor 6.

Figure 15:
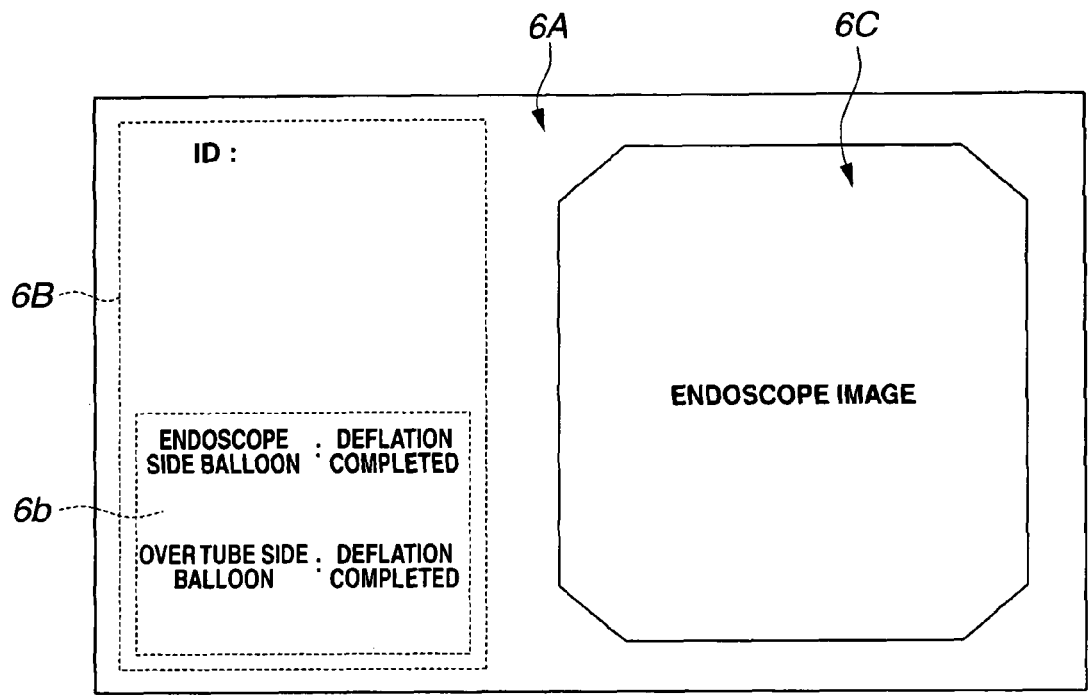

The image display example based on the composed image signal by the monitor in this case is shown in FIG. 15. That is, as shown in FIG. 15, a screen 6A of the monitor 6 is divided into two areas for display, for example, of a first screen 6B of an area displaying the endoscope balloon information image 6b and a second screen 6C displaying the endoscope image. The first screen 6B has an area for displaying patient information such as patient ID and the like placed at an upper part and the area 6b displaying the endoscope balloon information image placed at a lower part.

The endoscope balloon information image displayed in the area 6b is constituted by a character image corresponding to the name of the "endoscope-side balloon" and the "overtube side balloon" and a character image indicating the operating state of the balloons applicable to this character image such as the operating state of "deflation completed" of the endoscope side balloon 9 and "deflation completed" of the overtube side balloon 11, for example.

The endoscope balloon information image is not limited to character images but patterns such as icons may be used for display.

In this way, the endoscope balloon control device 7 of this embodiment performs 2-screen display of the first and the second screens 6B, 6C, for example, on the screen 6A of the monitor 6 by signal processing by the video processor 5 and displays the endoscope image (endoscope live image) on the second screen 6C at the same time as display of the endoscope balloon information image on the first screen 6B.

Next, action of the endoscope balloon control device of this embodiment will be described referring to FIGS. 15 to 26. The basic operating state of the endoscope system 1 is the same as that of the above first embodiment. Therefore, the display control operation by the endoscope balloon control device 7 of this embodiment will be described in correspondence to FIGS. 5 to 11 described in the above first embodiment.

When the operator conducts an endoscope inspection of a digestive tract using the endoscope system 1 in FIG. 1, the power button 22 of the remote controller 8 shown in FIG. 3 (or the power switch 17 shown in FIG. 2) is pressed down. Then, the control portion 35 of the endoscope balloon control device 7 starts the program shown in FIG. 12 as with the above first embodiment and performs driving control of the respective balloons 9, 11 and the display control of the monitor 6.

As shown in FIG. 5, when the operator inserts the endoscope 2 into the overtube 3, the balloon 9 of the endoscope 2 and the balloon 11 of the overtube 3 are drained of the air inside and deflated, and the operator starts insertion of the endoscope 2 to a subject in this state.

At this time, as shown in FIG. 15, the endoscope balloon control device 7 displays the endoscope balloon information image showing "endoscope side balloon"→"deflation completed", "overtube side balloon"→"deflation completed" on the first screen 6B on the screen 6A of the monitor 6 and displays the endoscope image on the second screen 6C at the same time. The monitor screen 6A similar to the above (See FIG. 15) is also displayed at the power on and the initialization of the endoscope balloon control device 7. Also, in this embodiment, since the endoscope image (endoscope live image) is displayed on the second screen 6C all the time, the subsequent description will be omitted for simplification of the description.

Next, the operator inserts the tip ends of the endoscope 2 and the overtube 3 to the duodenum descending limb, for example, and then, presses down the inflation/deflation button 20b on the overtube side of the remote controller 8 (See FIG. 3) to supply air from the second pump 32b to the balloon 11 for fixing the main body mounted at the tip end of the overtube 3, inflate this balloon 11 and fix the overtube 3 to the intestinal tract 40 as shown in FIG. 6.

Figure 16:
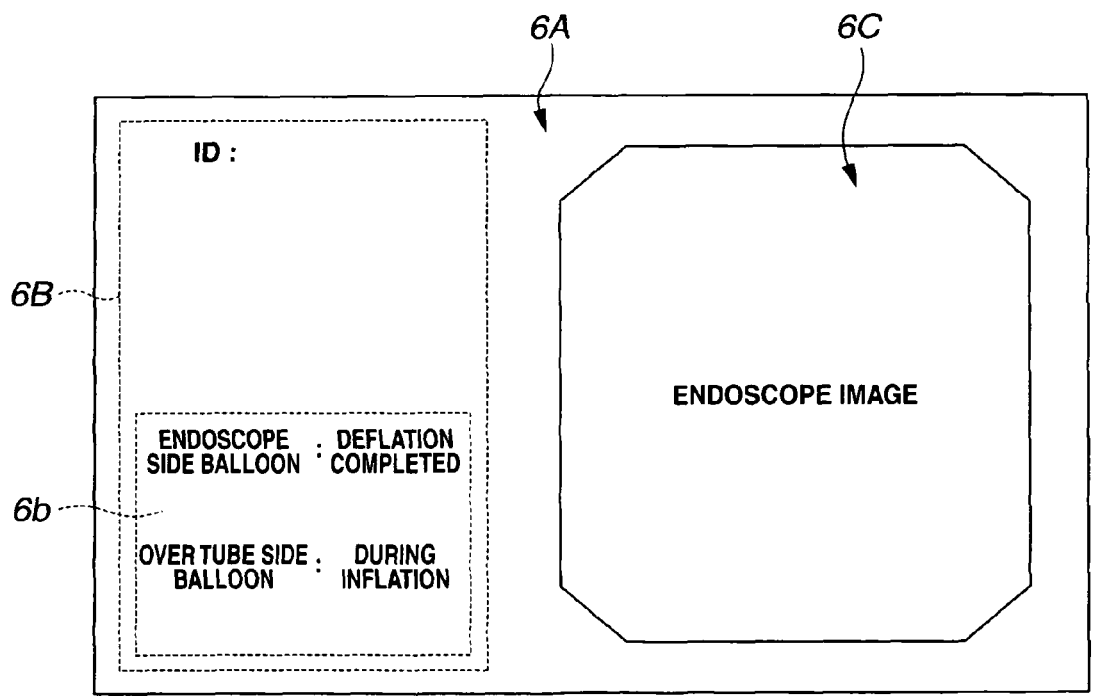
Figure 17:
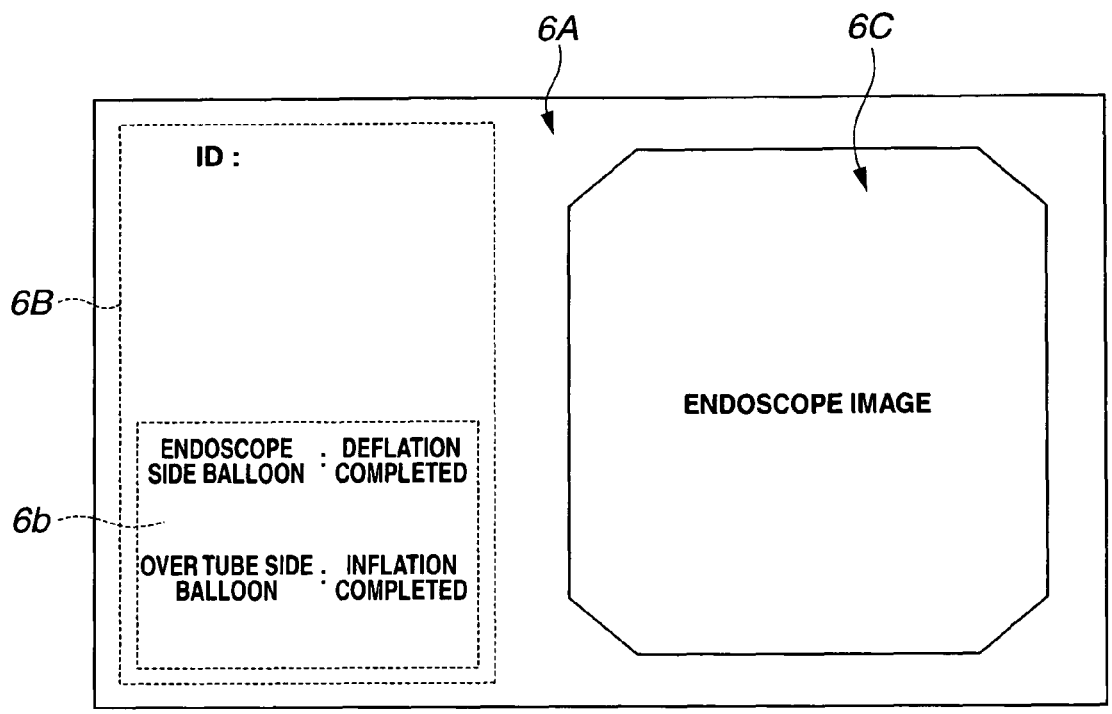

In this case, the endoscope balloon control device 7 displays the endoscope balloon information image 6b indicating "endoscope side balloon"→"deflation completed", "overtube side balloon"→"during inflation" on the first screen 6B on the screen 6A of the monitor 6 as shown in FIG. 16 at air supply of the balloon 11. And when air supply to the balloon 11 is completed and the balloon 11 is inflated into a desired state and fixed to the intestinal tract 40, the endoscope balloon control device 7 displays the endoscope balloon information image indicating "endoscope side balloon"→"deflation completed", "overtube side balloon"→"inflation completed" on the first screen 6B on the screen 6A of the monitor 6 as shown in FIG. 17.

Next, the operator maintains the overtube 3 with respect to the intestinal tract 40 and inserts only the insertion portion 2B of the endoscope 2 to the deep portion as shown in FIG. 7.

And while the insertion portion 2B of the endoscope 2 is inserted by a predetermined distance, the operator presses down the inflation/deflation button 20a on the endoscope side of the remote controller 8 (See FIG. 3) so as to supply air from the first pump 32a into the balloon 9 for fixing the main body mounted at the tip end of the endoscope 2 to inflate the balloon 9 and fix it to the intestinal tract 41 as shown in FIG. 8.

Figure 18:
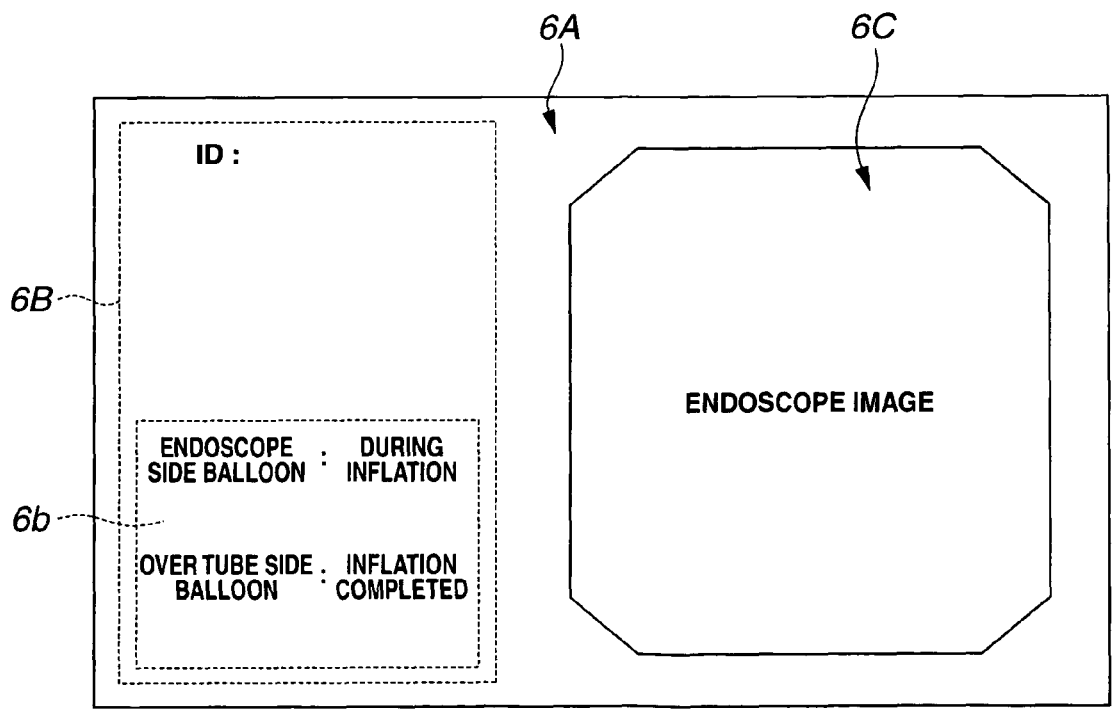
Figure 19:
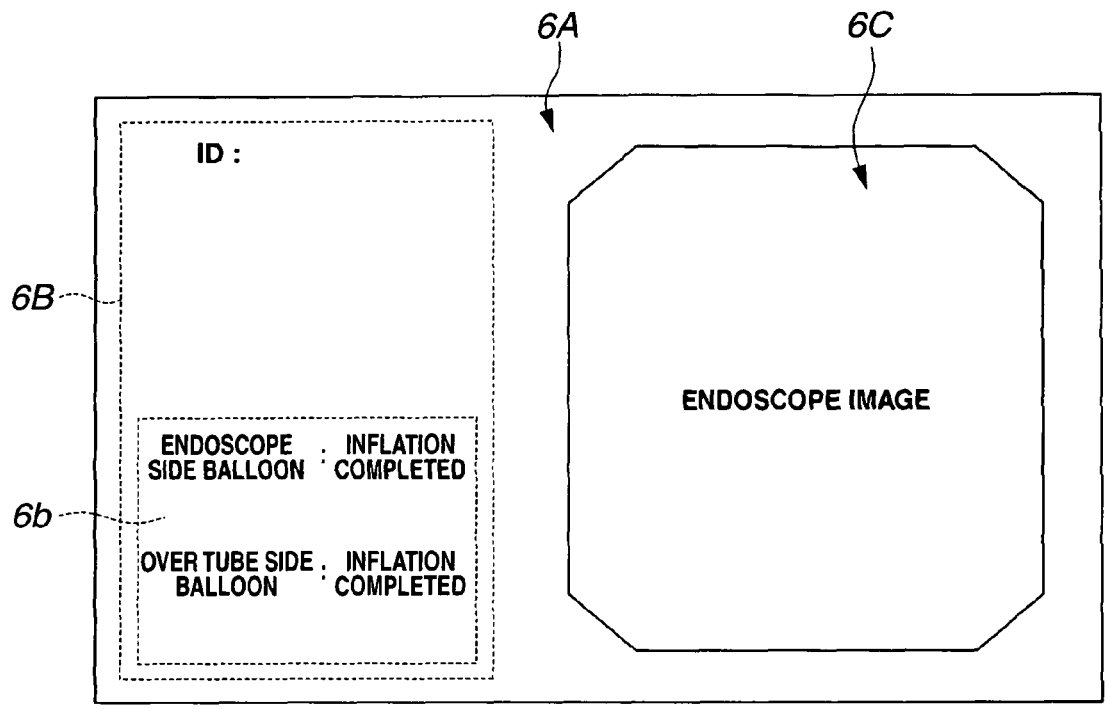

In this case, the endoscope balloon control device 7 displays the endoscope balloon information image 6b indicating "endoscope side balloon"→"during inflation", "overtube side balloon"→"inflation completed" on the first screen 6B on the screen 6A of the monitor 6 as shown in FIG. 18 at air supply to the balloon 9. And when the air supply to the balloon 9 is finished and the balloon 9 is fixed to the intestinal tract 41, the endoscope balloon control device 7 displays the endoscope balloon information image indicating "endoscope side balloon"→"inflation completed", "overtube side balloon"→"inflation completed" on the first screen 6B on the screen 6A of the monitor 6 as shown in FIG. 19.

Next, the operator presses down the inflation/deflation button 20b on the overtube side of the remote controller 8 (See FIG. 3) to release air in the balloon 11 by the pipeline switching portion 33, suction air in the balloon 11 of the overtube 3 from the second pump 32b and deflate the balloon 11 (See FIG. 9).

Figure 20:
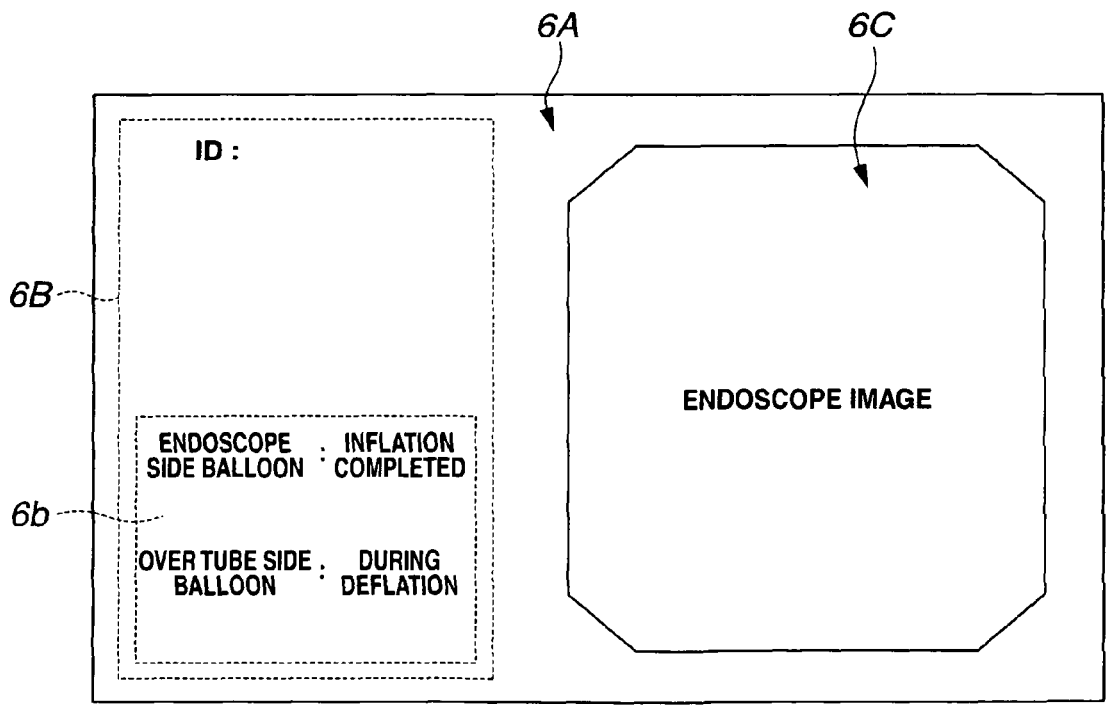
Figure 21:
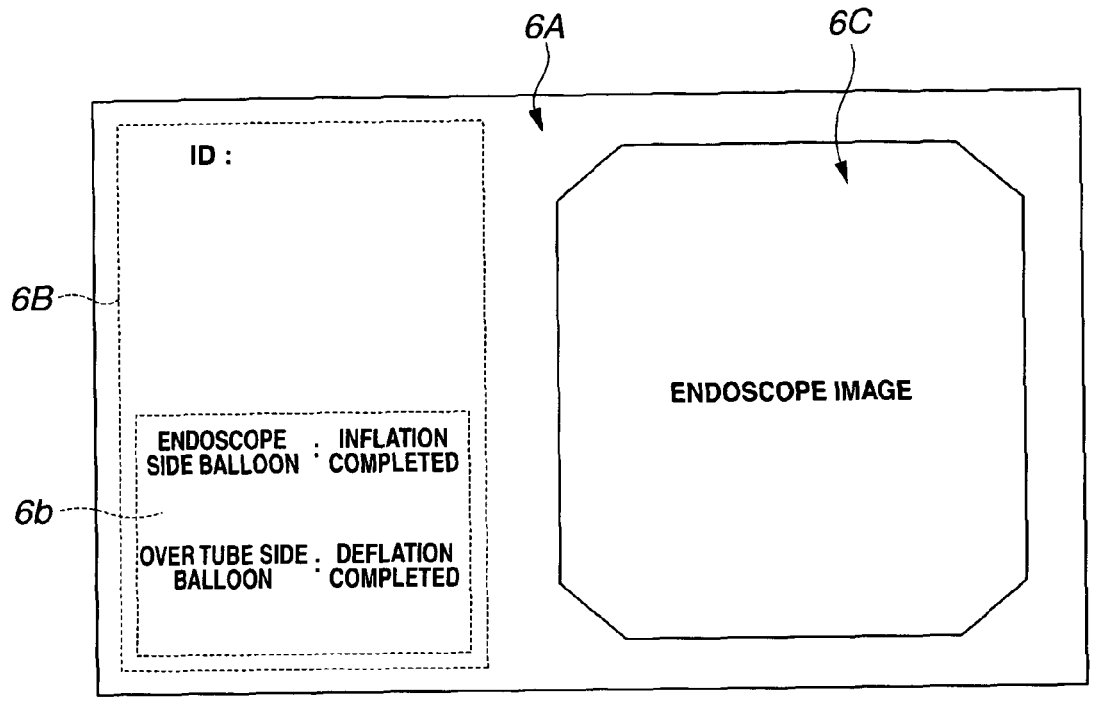

In this case, the endoscope balloon control device 7 displays the endoscope balloon information image 6b indicating "endoscope side balloon"→"inflation completed", "overtube side balloon"→"during deflation" on the first screen 6B on the screen 6A of the monitor 6 as shown in FIG. 20 at air suction of the balloon 11. And when air suction of the balloon 11 is finished, the endoscope balloon control device 7 displays the endoscope balloon information image indicating "endoscope side balloon"→"inflation completed", "overtube side balloon"→"deflation completed" on the first screen 6B on the screen 6A of the monitor 6 as shown in FIG. 21.

Then, the operator inserts the overtube 3 as shown in FIG. 9 along the endoscope 2 into the deep portion and inserts the tip end of the overtube 3 close to the tip end of the insertion portion 2B of the endoscope 2.

And in the state where the tip end of the overtube 3 is inserted close to the tip end of the insertion portion 2B, the operator presses down the inflation/deflation button 20b on the overtube side of the remote controller 8 (See FIG. 3) to supply air from the second pump 32b to the balloon 11 of the overtube 3, inflate this balloon 11 and fix the overtube 3 to the intestinal wall 41.

Figure 22:
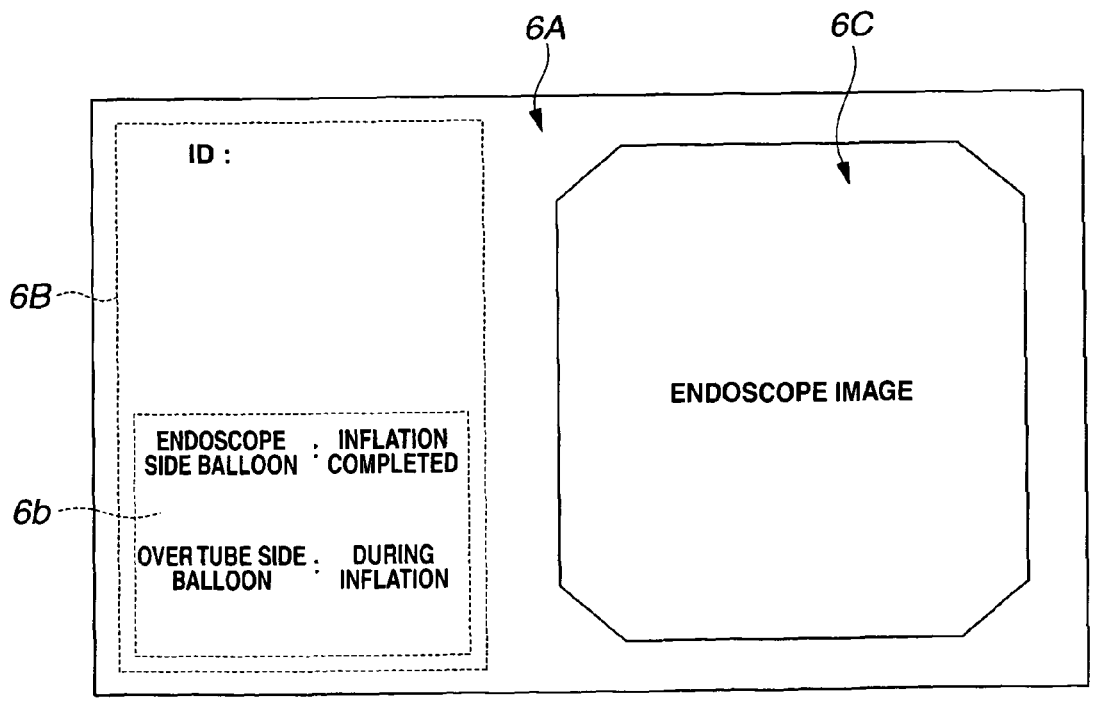
Figure 23:
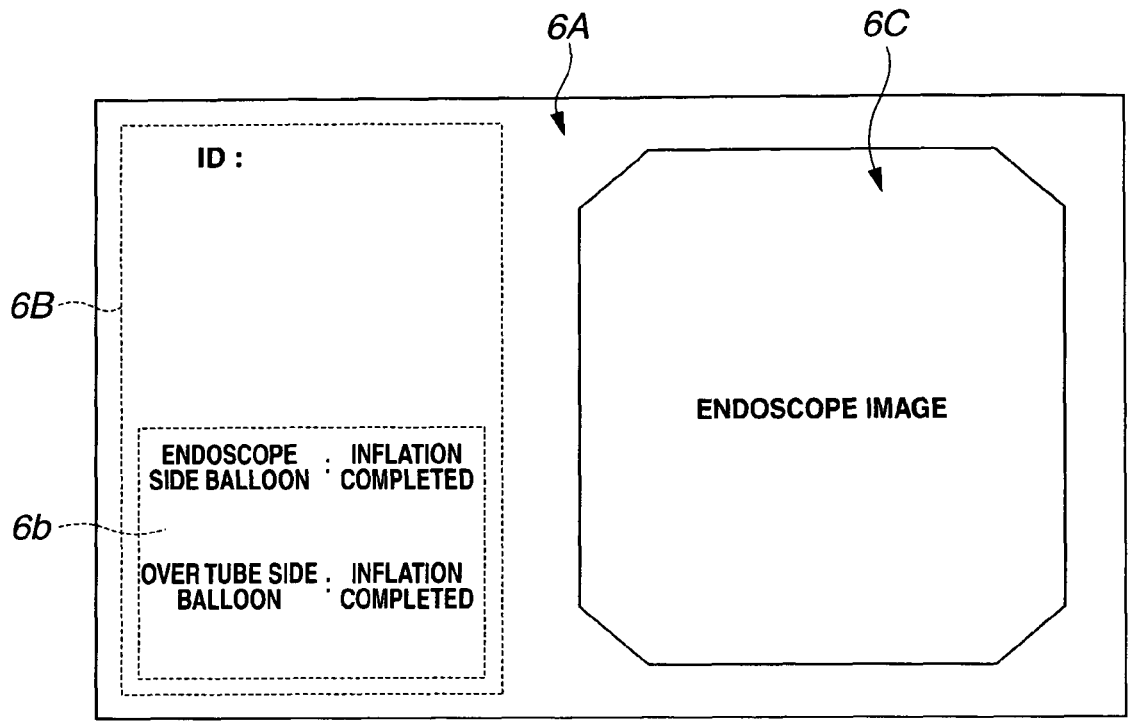

In this case, the endoscope balloon control device 7 displays the endoscope balloon information image 6b indicating "endoscope side balloon"→"inflation completed", "overtube side balloon"→"during inflation" on the first screen 6B on the screen 6A of the monitor 6 as shown in FIG. 22 at air supply to the balloon 11. And when the air supply to the balloon 11 is finished and the balloon 11 is inflated to a desired state and fixed to the intestinal tract 41, the endoscope balloon control device 7 displays the endoscope balloon information image indicating "endoscope side balloon"→"inflation completed", "overtube side balloon"→"inflation completed" on the first screen 6B on the screen 6A of the monitor 6 as shown in FIG. 23.

After that, the operator presses down the inflation/deflation button 20a on the endoscope side of the remote controller 8 (See FIG. 3) to release air in the balloon 9 by the pipeline switching portion 33, suction the air in the balloon 9 of the endoscope 2 from the first pump 32a, deflate the balloon 9 and further insert the insertion portion 2B to the deep portion.

Figure 24:
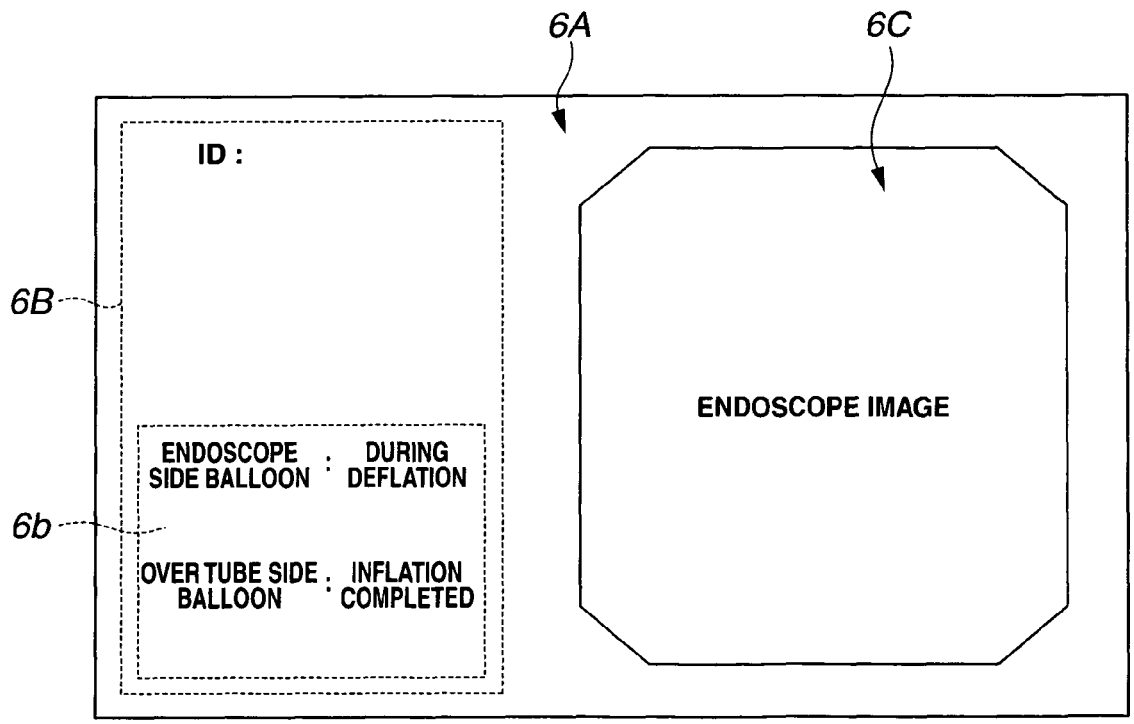

In this case, the endoscope balloon control device 7 displays the endoscope balloon information image 6b indicating "endoscope side balloon"→"during deflation", "overtube side balloon"→"inflation completed" on the first screen 6B on the screen 6A of the monitor 6 as shown in FIG. 24 at air suction of the balloon 9. And when the air suction of the balloon 9 is finished, the endoscope balloon control device 7 displays the endoscope balloon information image 6b indicating "endoscope side balloon"→"deflation completed", "overtube side balloon"→"inflation completed" on the first screen 6B on the screen 6A of the monitor 6 as shown in FIG. 25.

By repeating the above operation from FIG. 5 to FIG. 11, the insertion into the deep portion of the endoscope 2 and the overtube 3 is advanced, but the endoscope balloon control device 7 of this embodiment displays the operating states of the respective balloons 9, 11 according to their manipulated states on the screen 6A of the monitor 6 together with the endoscope image as shown in FIGS. 15 to 25.

Also, in this embodiment, when the emergency stop button 23 of the remote controller 8 (See FIG. 3) is pressed down by the operator during operation of the above endoscope system 1, the endoscope balloon control device 7 displays the endoscope balloon information image indicating "endoscope side balloon"→""during deflation", "overtube side balloon"→"during deflation" on the first screen 6B on the screen 6A of the monitor 6 and the endoscope image on the second screen 6C and newly displays a warning such as "over air-supply emergency stop" at the area 6X of the first screen 6B as shown in FIG. 26.

The warning character display may be flashed to surely notify the operator or may be displayed in a color different from the endoscope balloon information image.

Therefore, according to this embodiment, since the endoscope balloon information image indicating the operating states of the respective balloons 9, 11 can be displayed together with the endoscope image on the screen 6A of the monitor 6, the states of the respective balloons 9, 11 can be effectively recognized by the operator. The other effects are the same as those of the above first embodiment.

Since the endoscope balloon control device of the present invention can have the operator recognize the inflation states of the balloon of the endoscope and the balloon of the overtube, it is particularly effective in observation, treatment and the like of a deep portion and observation, treatment and the like of various portions of the deep portion using the respective balloons.

In the present invention, it is obvious that various embodiments in a wide range can be made on the basis of the present invention without deviating from the spirit and scope of the invention. The present invention is not limited by the specific embodiments other than the limitation by the appended claims.

What is claimed is:

1. An endoscope system comprising:
    a video processor for supplying an image data signal, obtained by signal processing an image pickup signal from an endoscope, to a monitor;
    a remote controller;
    an endoscope balloon control device connected to the remote controller, the endoscope balloon control device comprising:
        a first pump for supplying or discharging a gas to or from an endoscope side balloon arranged to an insertion portion of the endoscope;
        a first control portion for controlling a pressure in the endoscope side balloon; and
        a first inflation-state detection portion for detecting an inflation state of the endoscope side balloon on the basis of one or more of states of the first pump, a flow rate of the gas supplied to or discharged from the endoscope side balloon, and the pressure in the endoscope side balloon; and
    a first inflation-state information output portion provided at the video processor or the remote controller, the first inflation-state information output portion outputting, on the basis of the inflation state of the endoscope side balloon detected by the first inflation-state detecting portion, (i) information indicating one of an endo scope side balloon inflation mode and an endoscope side balloon deflation mode, and (ii) information indicating whether the endoscope balloon control device is in an operation state, the combination of which indicates the endoscope side balloon as being in one of an inflating state, an inflation completion state, a deflating state, and a deflation completion state.

2. The endoscope system according to claim 1, wherein the endoscope balloon control device further comprises:
    a second pump for supplying or discharging a gas to or from an overtube side balloon arranged to an overtube into which the endoscope is inserted;
    a second control portion for controlling a pressure in the overtube side balloon; and
    a second inflation-state detection portion for detecting an inflation state of the overtube side balloon on the basis of one or more of states of the second pump, a flow rate of the gas supplied or discharged to or from the overtube side balloon, and the pressure in the overtube side balloon; and
the endoscope system further comprises:
    a second inflation-state information output portion provided at the video processor or the remote controller, the second inflation-state information output portion outputting, on the basis of the inflation state of the overtube side balloon detected by the second inflation-state detecting portion, (i) information indicating one of an overtube side balloon inflation mode and an overtube side balloon deflation mode, and (ii) information indicating whether the endoscope balloon control device is in an operation state, the combination of which indicates the overtube side balloon as being in one of an inflating state, an inflation completion state, a deflating state, and a deflation completion state.

3. The endoscope system according to claim 1, further comprising a flow-rate adjusting portion for adjusting an air-supply or suction flow rate to or from the endoscope side balloon.

4. The endoscope system according to claim 2, further comprising a flow-rate adjusting portion for adjusting an air-supply or suction flow rate to or from the endoscope side balloon, the overtube side balloon, or both.

5. The endoscope system according to claim 2, wherein:
    an endoscope side balloon inflation/deflation button is provided on the remote controller for receiving an instruction from an operator for instructing the endoscope balloon control device to inflate/deflate the endoscope side balloon,
    a first inflation-state information display portion is provided on the remote controller, the first inflation-state information display portion being configured to display the information indicating one of the endoscope side balloon inflation mode and the endoscope side balloon deflation mode, and the information indicating whether the endoscope balloon control device is in the operation state.

6. The endoscope system according to claim 5, wherein:
    an overtube side balloon inflation/deflation button is provided on the remote controller for receiving an instruction from the operator for instructing the endoscope balloon control device to inflate/deflate the overtube side balloon,
    a second inflation-state information display portion is provided on the remote controller, the second inflation-state information display portion being configured to display the information indicating one of the overtube side balloon inflation mode and the overtube side balloon deflation mode, and the information indicating whether the endoscope balloon control device is in the operation state.

7. The endoscope system according to claim 1, wherein the inflation-state information output portion is configured to output the information indicating one of the endoscope side balloon inflation mode and the endoscope side balloon deflation mode, and the information indicating whether the endoscope balloon control device is in the operation state, to a display portion provided to the monitor.

8. The endoscope system according to claim 2, wherein the inflation-state information output portion is configured to output the information indicating one of the overtube side balloon inflation mode and the overtube side balloon deflation mode, and the information indicating whether the endoscope balloon control device is in the operation state to a display portion provided to the monitor.

9. The endoscope system according to claim 6, wherein a stop button is provided on the remote controller to receive an instruction from the operator for instructing the endoscope balloon control device to stop inflating/deflating the endoscope side balloon and the overtube side balloon.

10. The endoscope system according to claim 9, wherein the remote controller includes projections for preventing erroneous operation at an upper part and a lower part of an operation surface of the remote controller and the projections are set higher than a height of the endoscope side balloon inflation/deflation button, the overtube side balloon inflation/deflation button, and the stop button.

11. The endoscope system according to claim 3, wherein the flow-rate adjusting portion has at least one of an air-supply or suction flow-rate measuring portion and an air-supply or suction time measuring portion.

12. The endoscope system according to claim 4, wherein the flow-rate adjusting portion has at least one of an air-supply or suction flow-rate measuring portion and an air-supply or suction time measuring portion.

13. The endoscope system according to claim 2, wherein the video processor is configured to compose a combined image signal on the basis of the image data signal, the information indicating one of the endoscope side balloon inflation mode and the endoscope side balloon deflation mode, the information indicating one of the overtube side balloon inflation mode and the overtube side balloon deflation mode, and information indicating whether the endoscope balloon control device is in the operation state and to output the combined image signal to the monitor.

14. An endoscope system comprising:
   a video processor for supplying an image data signal, obtained by signal processing an image pickup signal from an endoscope, to a monitor;
   a remote controller
   a balloon control device comprising:
      a pump for supplying or discharging a gas to or from a balloon mounted at an outer circumference portion at a tip end portion of an overtube in which the endoscope is inserted;
      a control portion for controlling a pressure in the balloon of the overtube; and
      an inflation-state detection portion for detecting an inflation state of the balloon of the overtube on the basis of one or more of states of the pump, a flow rate of the gas supplied to or discharged from the balloon, and the pressure in the balloon; and
      an inflation-state information output portion provided at the video processor or the remote controller, the inflation-state information output portion outputting, on the basis of the inflation state detected by the inflation-state detecting portion, (i) information indicating one of a balloon inflation mode and a balloon deflation mode, and (ii) information indicating whether the balloon control device is in an operation state, the combination of which indicates the balloon as being in one of an inflating state, an inflation completion state, a deflating state, and a deflation completion state.

15. The endoscope system according to claim 14, further comprising a flow-rate adjusting portion for adjusting an air-supply or suction flow rate to or from the balloon.

16. The endoscope system according to claim 14, wherein the remote controller includes:
   an inflation/deflation operation button for receiving an instruction from an operator for instructing the balloon control device to inflate/deflate the balloon, and
   a display portion for displaying the information indicating one of the balloon inflation mode and the balloon deflation mode, and the information indicating whether the balloon control device is in the operation state.

17. The endoscope system according to claim 16, wherein the remote controller further includes projections for preventing erroneous operation at an upper part and a lower part of an operation surface of the remote controller and the projections are set higher than the height of the inflation/deflation operation button.

18. The endoscope system according to claim 15, wherein the flow-rate adjusting portion has at least one of an air-supply or suction flow-rate measuring portion and an air-supply or suction time measuring portion.

19. The endoscope system according to claim 14, wherein the video processor is configured to compose a combined image signal on the basis of the image data signal, the information indicating one of a balloon inflation mode and a balloon deflation mode, and information indicating whether the balloon control device is in the operation state, and to output the combined image signal to the monitor.

* * * * *

UNITED STATES PATENT AND TRADEMARK OFFICE
CERTIFICATE OF CORRECTION

PATENT NO. : 8,096,942 B2
APPLICATION NO. : 11/545678
DATED : January 17, 2012
INVENTOR(S) : Takatoshi Yoshida et al.

It is certified that error appears in the above-identified patent and that said Letters Patent is hereby corrected as shown below:

Column 17, line 41 (claim 1, line 25) should read: tion, (i) information indicating one of an endoscope side Signed and Sealed this
Eighteenth Day of September, 2012

David J. Kappos
*Director of the United States Patent and Trademark Office*